(12) United States Patent
Shelton et al.

(10) Patent No.: US 10,794,889 B2
(45) Date of Patent: Oct. 6, 2020

(54) MULTISPECTRAL THERMAL IMAGING FOR DETECTION OF MATERIALS OF INTEREST

(71) Applicant: FLIR Detection, Inc., Stillwater, OK (US)

(72) Inventors: Robert K. Shelton, Stillwater, OK (US); Brian D. O'Dell, Stillwater, OK (US); Shiou-Jyh Ja, Stillwater, OK (US)

(73) Assignee: FLIR DETECTION, INC., Stillwater, OK (US)

( * ) Notice: Subject to any disclaimer, the term of this patent is extended or adjusted under 35 U.S.C. 154(b) by 0 days.

(21) Appl. No.: 15/638,287

(22) Filed: Jun. 29, 2017

(65) Prior Publication Data
US 2018/0003689 A1    Jan. 4, 2018

Related U.S. Application Data

(60) Provisional application No. 62/357,212, filed on Jun. 30, 2016.

(51) Int. Cl.
*G01J 3/00* (2006.01)
*G01N 33/22* (2006.01)
(Continued)

(52) U.S. Cl.
CPC .............. *G01N 33/22* (2013.01); *G01N 21/35* (2013.01); *G01N 21/3504* (2013.01);
(Continued)

(58) Field of Classification Search
CPC .. G01N 21/35; G01N 21/359; G01N 21/3504; G01J 3/02; G01J 3/42
See application file for complete search history.

(56) References Cited

U.S. PATENT DOCUMENTS 5,092,156 A * 3/1992 Miskolczy ............... G01N 1/02
436/156
6,558,626 B1   5/2003 Aker et al.
(Continued)

FOREIGN PATENT DOCUMENTS

CN            103502817        1/2014

OTHER PUBLICATIONS

Miller et al., "Infrared Spectra and Characteristic Frequencies of Inorganic Ions Their Use in Qualitative Analysis", Analytical Chemistry, Aug. 8, 1952, pp. 1253-1294, vol. 24, No. 8, Department of Research in Chemical Physics, Mellon Institute, Pittsburgh/U.S.

*Primary Examiner* — David P Porta
*Assistant Examiner* — Mamadou Faye
(74) *Attorney, Agent, or Firm* — Haynes and Boone, LLP

(57) ABSTRACT

Imaging techniques are provided to determine the presence of trace chemicals corresponding to various materials of interest. In one example, a method includes receiving a test sample and capturing a plurality of infrared images of the test sample. Each infrared image corresponds to a different range of infrared radiation wavelengths. The method also includes determining a spectral profile of the test sample using the infrared images, comparing the determined spectral profile to a known spectral profile of a material of interest, and determining whether the material is present in the test sample based on the comparing. Additional methods and related devices are also provided.

20 Claims, 18 Drawing Sheets

(51) Int. Cl.
  *G01N 21/35*      (2014.01)
  *G01N 21/3504*    (2014.01)
  *G01N 21/3563*    (2014.01)
  *G01N 33/00*      (2006.01)

(52) U.S. Cl.
  CPC ..... *G01N 21/3563* (2013.01); *G01N 33/0057* (2013.01); *G01N 2201/0221* (2013.01)

(56) References Cited

U.S. PATENT DOCUMENTS

| | | | |
|---|---|---|---|
| 6,883,452 B1 | 4/2005 | Gieseke | |
| 7,109,488 B2 | 9/2006 | Milton | |
| 7,208,122 B2 | 4/2007 | Swager et al. | |
| 7,393,503 B2 | 7/2008 | Swager et al. | |
| 7,419,636 B2 | 9/2008 | Aker et al. | |
| 7,623,234 B2 * | 11/2009 | Puzey | C12Q 1/04 356/326 |
| 7,645,069 B1 | 1/2010 | Fine et al. | |
| 7,662,309 B2 | 2/2010 | Swager et al. | |
| 7,943,062 B2 | 5/2011 | Swager et al. | |
| 8,292,496 B1 | 10/2012 | Fine et al. | |
| 8,323,576 B2 | 12/2012 | Aker et al. | |
| 8,379,208 B1 | 2/2013 | Simmons et al. | |
| 8,465,678 B2 | 6/2013 | Swager et al. | |
| 8,477,311 B2 | 7/2013 | Russell | |
| 8,647,579 B2 | 2/2014 | La Grone et al. | |
| 9,005,524 B2 | 4/2015 | Deans et al. | |
| 9,068,960 B2 | 6/2015 | Wald et al. | |
| 9,588,091 B2 | 3/2017 | Wald et al. | |
| 2004/0157342 A1 * | 8/2004 | Lovell | G01N 1/2202 436/173 |
| 2007/0086925 A1 * | 4/2007 | O'Donnell | G01N 1/2214 422/82.05 |
| 2010/0044570 A1 * | 2/2010 | McGill | G01N 21/71 250/338.5 |
| 2010/0211333 A1 | 8/2010 | Pruet et al. | |
| 2011/0012916 A1 * | 1/2011 | Nelson | G01J 3/02 345/593 |
| 2011/0271738 A1 * | 11/2011 | McGill | G01N 21/64 73/23.41 |
| 2012/0007979 A1 | 1/2012 | Schneider et al. | |
| 2012/0134582 A1 * | 5/2012 | Treado | G01J 3/28 382/165 |
| 2012/0261578 A1 | 10/2012 | Scott et al. | |
| 2013/0341509 A1 * | 12/2013 | Nelson | G01J 3/0248 250/330 |
| 2014/0017803 A1 | 1/2014 | Deans et al. | |

\* cited by examiner

1900 →

2000 →

MULTISPECTRAL THERMAL IMAGING FOR DETECTION OF MATERIALS OF INTEREST

CROSS-REFERENCE TO RELATED APPLICATIONS

This application claims the benefit of U.S. Provisional Patent Application No. 62/357,212 filed Jun. 30, 2016 and entitled "MULTISPECTRAL THERMAL IMAGING FOR DETECTION OF MATERIALS OF INTEREST" which is hereby incorporated by reference in its entirety.

TECHNICAL FIELD

The present invention relates generally to chemical detection and, more particularly, to the detection of trace materials of interest.

BACKGROUND

To reduce threats associated with hidden explosives, various detection devices have been developed. Typically, such devices are implemented using vapor-based systems. In these systems, trace amounts of a sample are vaporized and physically collected by a detector to determine a chemical composition of the sample.

Although such vapor-based techniques are highly effective in detecting many types of explosive materials, certain other types of explosive materials are not easily detected using this approach. For example, oxidizing materials are a component of a common class of homemade explosives which pose certain challenges to conventional vapor-based systems.

In this regard, many oxidizing materials (e.g., oxidizing salts such as nitrates, chlorates, perchlorates, permanganates, dichromates, and other materials) typically exhibit very low vapor pressures at room temperature, and heating such materials to high temperatures where they would melt, boil, or otherwise decompose generates no uniquely identifiable vapor signature. As a result, such materials typically have insufficient usable vapor present to interact with conventional chemical detectors. Therefore, even when extremely sensitive vapor-based detection systems are used at high vaporization temperatures, conventional detection systems are unable to provide an unambiguous detection result for such materials.

Although complex spectroscopy techniques are used in laboratory environments to detect the chemical content of certain materials, such conventional spectroscopy techniques are impractical for the detection of explosive materials in the field. For example, conventional spectrometers used in analytical chemistry laboratories typically rely on computationally-intensive Fourier Transforms to determine spectral content over many different wavebands. Although such spectrometers provide high resolution for detecting many classes of materials, they are costly and impractical for real world explosive detection scenarios where a limited number of materials need to be detected and where low cost, speed, and portability are important.

SUMMARY

Techniques are provided for capturing filtered images using various wavelengths to detect spectral features corresponding to materials of interest. Such techniques are particularly useful in the detection of explosive materials, but may be applied to other materials of interest where appropriate. In some embodiments, such imaging techniques may be combined with other vapor-phase chemical detection techniques to provide flexible detection methods and devices.

In one embodiment, a method includes receiving a test sample; capturing a plurality of infrared images of the test sample, wherein each infrared image corresponds to a different range of infrared radiation wavelengths; determining a spectral profile of the test sample using the infrared images; comparing the determined spectral profile to a known spectral profile of a material of interest; and determining whether the material is present in the test sample based on the comparing.

In another embodiment, a device includes a chamber configured to receive a test sample; an infrared imager configured to capture a plurality of infrared images of the test sample, wherein each infrared image corresponds to a different range of infrared radiation wavelengths; a plurality of filters configured to be positioned between the test sample and the infrared imager to filter the infrared radiation into the different ranges of infrared radiation wavelengths captured in the infrared images; a memory comprising instructions; and a processor configured to execute the instructions to: determine a spectral profile of the test sample using the infrared images, compare the determined spectral profile to a known spectral profile of a material of interest, and determine whether the material is present in the test sample based on the compared spectral profiles.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
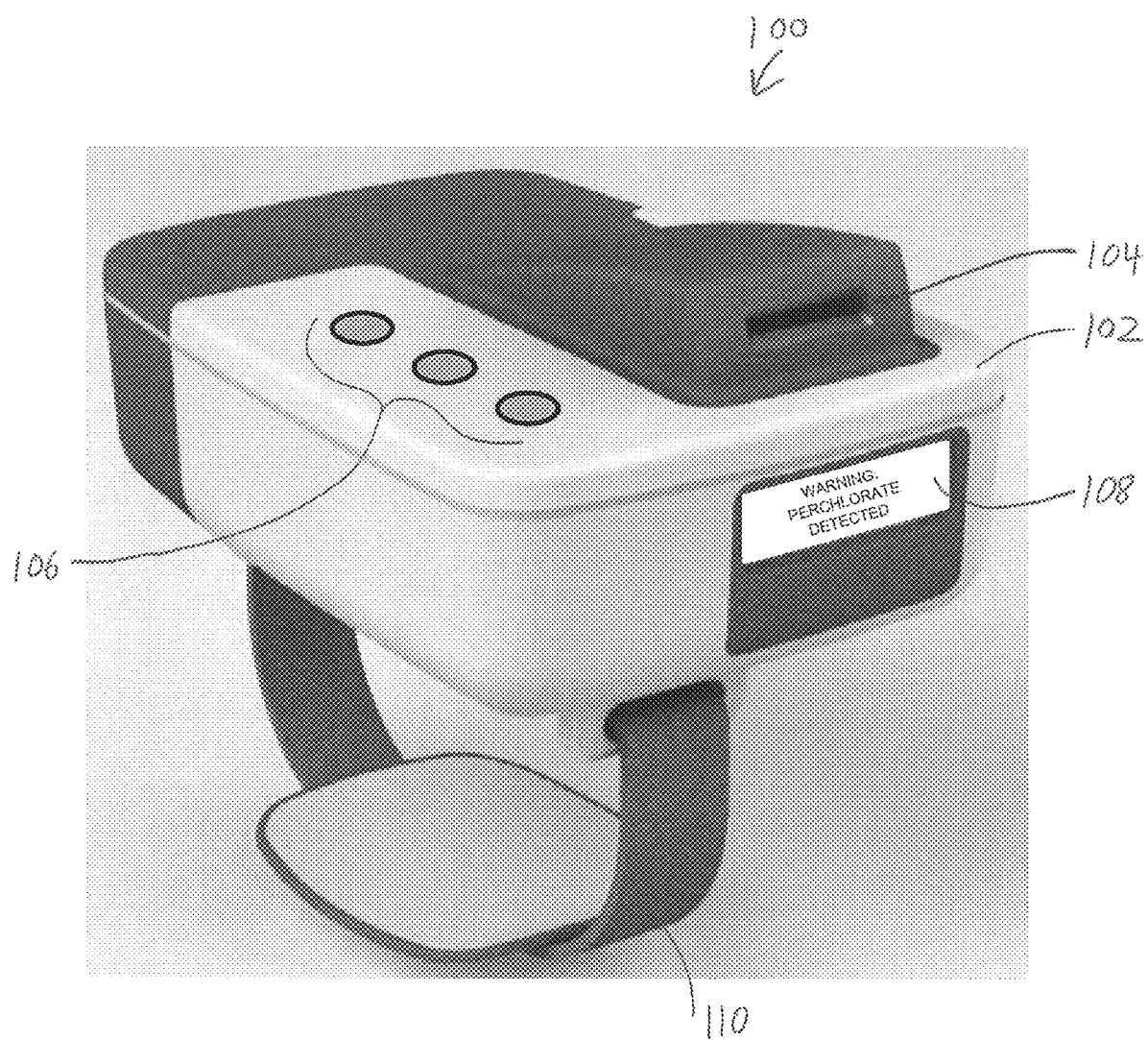
FIG. 1 illustrates an external view of a trace material detection device utilizing thermal imaging in accordance with an embodiment of the disclosure.

In accordance with various embodiments disclosed herein, devices and related methods are provided to detect the presence of trace chemicals corresponding to materials of interest using imaging techniques. In this regard, certain materials of interest may exhibit characteristic absorbance and/or emissivity responses corresponding to particular spectral profiles that may be used to identify certain classes of such materials.

Various thermal imaging techniques are provided in relation to the use of thermal images associated with various infrared wavelengths including, for example, mid-wavelength infrared (MWIR) radiation (e.g., from approximately 3 μm to approximately 8 μm) and/or long-wavelength infrared (LWIR) radiation (e.g., from approximately 8 μm to approximately 15 μm). Such techniques are particularly useful in the detection of explosive materials, but may be applied to other materials of interest where appropriate. In some embodiments, such thermal imaging techniques may be combined with other vapor-phase chemical detection techniques to provide flexible detection methods and devices.

Although thermal imaging techniques using MWIR radiation and/or LWIR radiation wavelength ranges are specifically identified, other wavelength ranges may be used including, but not limited to, short-wave infrared (SWIR) radiation (e.g., from approximately 1.4 μm to approximately 3 μm), near-infrared radiation (e.g., from approximately 0.75 μm to approximately 1.4 μm), visible light (e.g., from approximately 400 nm to approximately 700 μm), and/or others as desired. Accordingly, imaging devices and/or filters may be implemented as appropriate to apply the techniques discussed herein to any desired wavelength range (e.g., infrared, visible light, and/or others).

Although certain materials of interest such as oxidizing salts and explosive materials are specifically discussed herein, the various techniques of the present disclosure may be applied to a wide range of additional materials of interest. Such materials include, but are not limited to, narcotics, chemical warfare agents, toxic industrial chemicals (TICs), illicit substances, and others as appropriate.

In accordance with various embodiments further discussed herein, thermal images may be captured of one or more test samples using a limited number of different ranges of thermal radiation wavelengths. For example, a small number of filters (e.g., 8 or fewer in some embodiments) may be positioned between the test samples and a thermal imager to capture thermal images corresponding to different ranges of thermal radiation wavelengths. In some embodiments, one or more additional thermal images may be generated from the captured images, for example, by selectively subtracting, adding, and/or otherwise combining captured images corresponding to different ranges to obtain one or more additional thermal images having additional different ranges.

By analyzing the intensity of the thermal radiation captured in the different thermal images for particular wavelength ranges, spectral profiles may be determined for the test samples. The determined spectral profiles may be compared to an existing library of known spectral profiles associated with materials of interest. By correlating the determined spectral profiles with one or more of the known spectral profiles, the test samples may be identified in a low cost, rapid, and highly portable manner to discriminate between various oxidizing and non-oxidizing materials. In some embodiments, these thermal techniques may detect materials in trace amounts as small as approximately 2 ng.

In some embodiments, such thermal imaging techniques may be combined with additional vapor-phase chemical detection techniques to provide methods and systems for detecting additional classes of materials. For example, certain oxidizing materials may be detected using the thermal imaging techniques, while other materials exhibiting detectable vapor pressures may be detected using a vapor-phase chemical detector.

Turning now to the drawings, FIG. 1 illustrates an external view of a trace material detection device 100 utilizing thermal imaging in accordance with an embodiment of the disclosure. For example, in some embodiments, device 100 may be implemented as a handheld portable detector capable of detecting explosives and/or other materials.

As shown, device 100 includes a housing 102, a slot 104, user controls 106, a display 108, and a strap 110. In various embodiments, additional components of device 100 (e.g., further illustrated in FIG. 2) may be distributed at physical locations internal to and/or external to housing 102.

In operation, sampling media may be brought into physical contact with one or more surfaces to be tested. For example, in some embodiments, a user may wipe the media (e.g., also referred to as a "swab" or "swipe" and further illustrated in FIG. 5) against a surface of interest to collect trace amounts of one or more test substances resident on the surface. The user then inserts the media into slot 104 after which additional operations and analysis are performed as further discussed herein. In some embodiments, the media may be implemented using an appropriate substrate such as polytetrafluoroethylene (PTFE), an aramid polymer, polyethylene, polyester, paper, and/or other materials.

User controls 106 receive user input to operate device 100. As shown in FIG. 1, user controls 106 may be implemented as physical buttons. In other embodiments, user controls 106 may be implemented by one or more keyboards, levers, joysticks, touchscreens, and/or other controls. In some embodiments, user controls 150 may be integrated with display 108 as a touchscreen.

Display 108 presents information to the user of device 100. For example, FIG. 1 illustrates a warning message provided on display 108 in response to a detected material. In various embodiments, display may be implemented as a liquid crystal display (LCD), an organic light emitting diode (OLED) display, and/or any other appropriate display.

Strap 110 may be used to secure device 100 to a user's body and/or a structure as desired for convenient placement and use in the field. Additional features of device 100 are further illustrated in FIG. 2.

Figure 2:
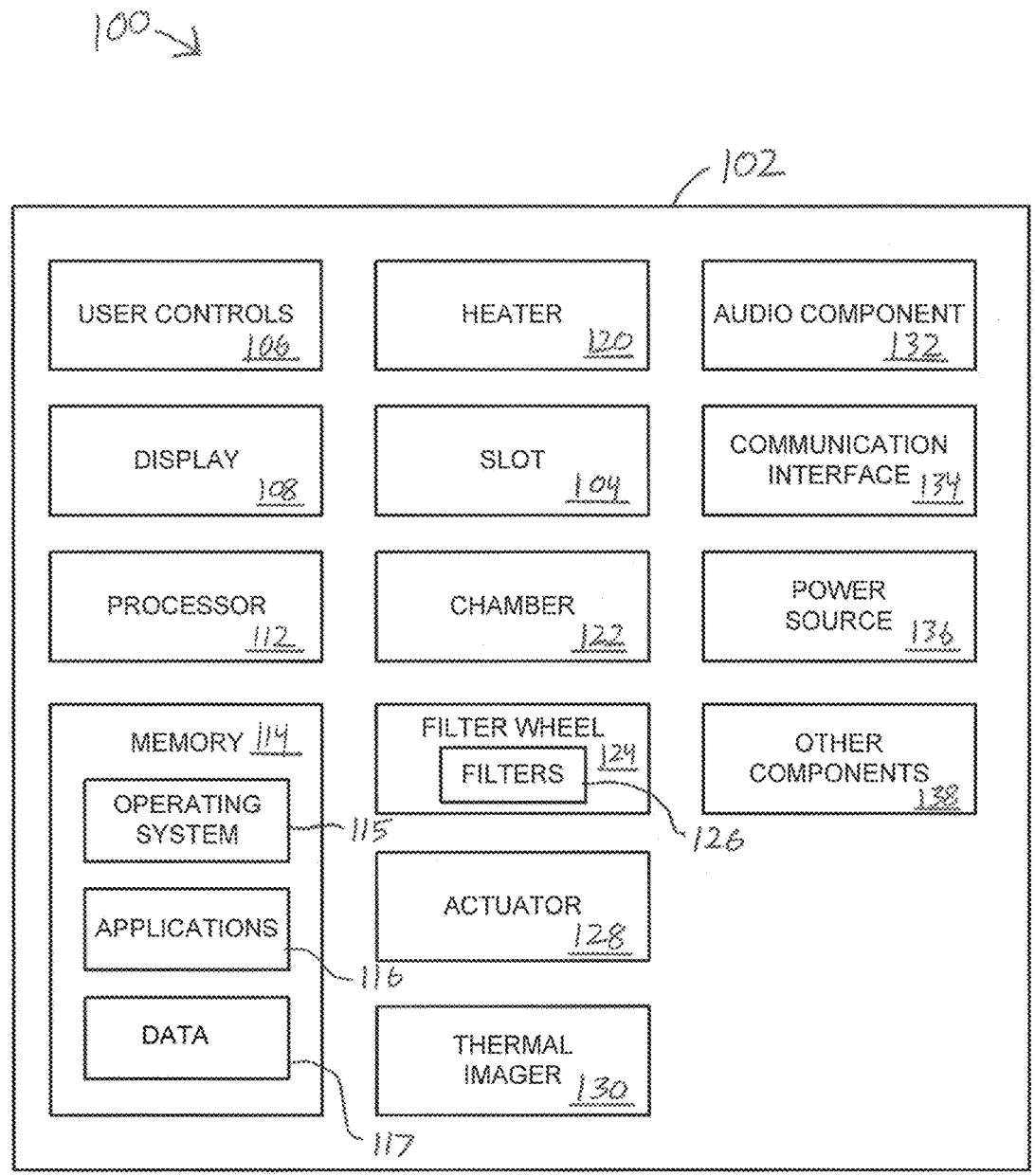
FIG. 2 illustrates a block diagram of a trace material detection device utilizing thermal imaging in accordance with an embodiment of the disclosure.

FIG. 2 illustrates a block diagram of device 100 in accordance with an embodiment of the disclosure. In addition to several previously discussed components shown in FIG. 1, FIG. 2 further illustrates a processor 112, a memory 114, a heater 120, a chamber 122, a filter wheel 124, an actuator 128, a thermal imager 130, an audio component 132, a communication interface 134, a power source 136, and other components 138.

Processor 112 may be implemented as one or more microprocessors, microcontrollers, system on a chip (SoC), application specific integrated circuits (ASICs), programmable logic devices (PLDs) such as field programmable gate arrays (FPGAs), complex programmable logic devices (CPLDs), field programmable systems on a chip (FPSCs), etc., or other processing devices used to control the operations of device 100. In this regard, processor 112 may execute machine readable instructions (e.g., software, firmware, or other instructions) stored in memory 114.

Memory 114 may be implemented as a machine readable medium storing various machine readable instructions and data. For example, in some embodiments, memory 114 may store an operating system 115, and one or more applications 116 as machine readable instructions that may be read and executed by processor 112 to perform various operations described herein. Memory 114 may also store various types of data 117 including, for example, thermal images, spectral profiles, test sample identification results, and/or other information used or provided by the various components of device 100. In various embodiments, memory 114 may be implemented to store such instructions and data in a non-transitory manner and/or may be implemented with both transitory and non-transitory portions to selectively store all or portions of such instructions and data in either manner as appropriate.

Heater 120 may be used to heat test samples (e.g., provided on media as discussed) to a desired temperature such that the test samples emits sufficient thermal radiation to be captured in thermal images. In some embodiments, heater 120 may be a resistive heater configured to heat the test samples, however other configurations may be used in other embodiments.

Chamber 122 provides a recessed volume within housing 102 and receives the media inserted through slot 104. While disposed in chamber 122, the media may be heated by heater 120 and thermally imaged by thermal imager 130 as further discussed herein.

Filter wheel 124 may be selectively rotated by actuator 128 in response to control signals provided by, for example, processor 112. In this regard, filter wheel 124 includes various filters 126 which may be selectively positioned between the media and thermal imager 130 to filter the thermal radiation emitted from the test sample and captured by thermal imager 130.

Although a filter wheel 124 is illustrated and described, this is merely one contemplated implementation. For example, in other embodiments, filters 126 may be selectively positioned through other types of mechanisms and/or manual operations performed by a user. In still other embodiments, one or more of filters 126 may be maintained in fixed positions, and thermal imager 130 may capture an image having differently filtered regions (e.g., to filter multiple wavelength ranges in a single image). In other embodiments, thermal imager 130 may be implemented by a plurality of image capture devices each having a corresponding array of infrared sensors and each being associated with a different filter 126, as further discussed with regard to FIG. 5.

Thermal imager 130 may be implemented with an array of infrared sensors (e.g., microbolometers and/or other types of thermal detectors) provided as a unit cell array configured to capture thermal images of thermal radiation received from test samples in chamber 122. In various embodiments, thermal imager 130 may capture thermal radiation in MWIR and/or LWIR wavelength ranges. In this regard, thermal imager 130 may also be implemented with various support circuitry such as a read out integrated circuit (ROIC) (e.g., including bias generation and timing control circuitry, row/column amplifiers, row/column multiplexers, output amplifiers, and/or other components as appropriate. Accordingly, thermal imager 130 provides captured thermal images to processor 112 and/or memory 114 for further use and operation by device 100. Further descriptions of ROICs and infrared sensors (e.g., microbolometer circuits) may be found in U.S. Pat. No. 6,028,309 issued Feb. 22, 2000, which is incorporated herein by reference in its entirety. Although thermal imager 130 and thermal imager 330 (further discussed herein) are particularly referenced by the present disclosure, other types of imagers such as infrared imagers, visible light imagers, and/or others may be used as appropriate to capture images of various desired wavelengths as discussed.

Audio component 132 may be implemented, for example, as a speaker or other transducer with corresponding driver circuitry to provide audible sounds to a user of device 100. For example, in some embodiments, audio component 132 may provide audible signals in response to manipulation of user controls 106 and/or in response to the operations of processor 112 (e.g., to indicate that a particular material is present or is not present).

Communication interface 134 may be implemented as a wired and/or wireless interface connect device 100 (e.g., by Universal Serial Bus (USB), Ethernet, WiFi, Bluetooth, cellular, infrared, radio, and/or other protocols) with various external devices to update operating system 115, update applications 116, and/or communicate data 117. In some embodiments, communication interface 134 may connect to external power sources (e.g., a power outlet) to charge a battery of power source 136 and/or to directly power device 100.

Power source 136 may be implemented, for example, as a battery to permit mobile and remote use of device 100. In some embodiments, power source 136 may be a removable battery. Other components 138 may also be provided as appropriate for various types of devices 100 to support, for example, application specific operations of such devices. In some embodiments, one or more additional imagers (e.g., infrared imagers, visible light imagers, and/or others) may be provided as part of other components 138 to capture additional images as desired. For example, in some embodiments, a visible light imager may be used to provide one or more reference images for performing image registration operations in relation to captured thermal images.

As discussed, in some embodiments, thermal imaging techniques may be combined with additional vapor-phase chemical detection techniques to permit detection of additional classes of materials. For example, certain standard military explosives (e.g., trinitrotoluene (TNT), Research Department explosive (RDX), pentaerythritol tetranitrate (PETN), and others) do not have high vapor pressures at room temperature, but still have much more vapor pressure than oxidizing salts. Heating such standard military explosives (e.g., to temperatures in the range of approximately 90 degrees C. to approximately 160 degrees C.), provides sufficient vapor to be successfully detected using a media-based thermal desorber as discussed, whereas many oxidizing salts will not.

In this regard, the following Table 1 identifies vapor pressures, melting temperatures, and boiling (e.g., vaporization) temperatures associated with various materials, including ultra-low vapor pressure materials (e.g., sodium perchlorate and potassium chlorate), low vapor pressure materials (e.g., RDX and TNT), medium vapor pressure materials (e.g., glycerol), and high vapor pressure materials (e.g., ethanol). As set forth in Table 1, the identified melting and boiling temperatures are generally inversely proportional to the identified vapor pressures and provide a useful indicator for the expected vapor pressure of a given material.

314 (including operating system 315, applications 316, and data 317), a heater 320, a chamber 322, a filter wheel 324 (including filters 326), an actuator 328, a thermal imager 330, an audio component 332, a communication interface 334, a power source 336, and other components 338, all of which may be implemented in the same or similar manner as corresponding components of device 100 previously discussed. As shown, FIG. 4 also illustrates a transfer tube 340, a pump 342, and a chemical detector 344 (e.g., implemented as a mass spectrometer (MS), ion mobility spectrometer (IMS), fluorescence-based detector, colorimetric detector, and/or using other technologies) that may be used with heater 320 to provide a media-based thermal desorber to perform vapor-based material detection as further discussed herein.

Figure 5:
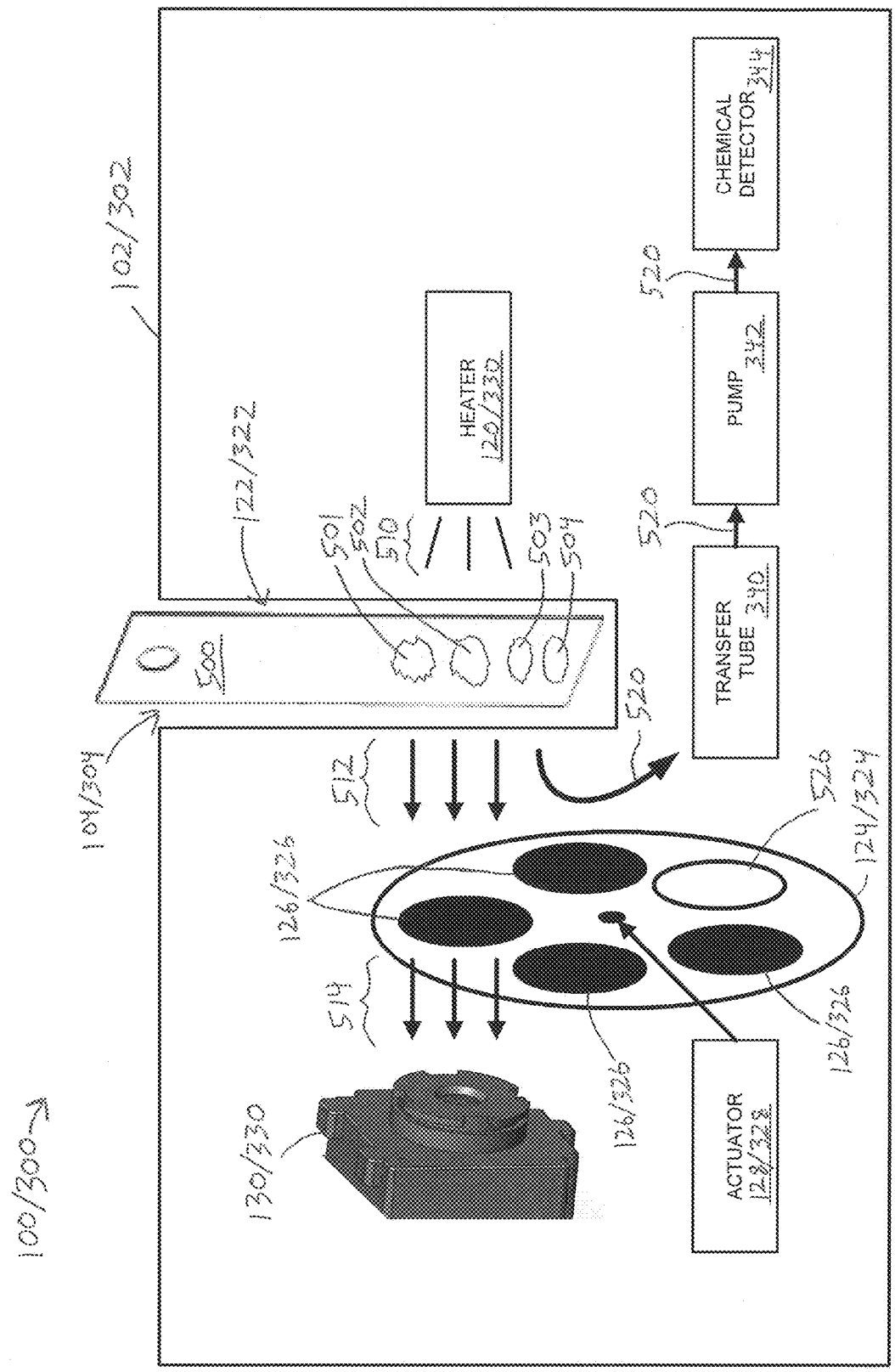
FIG. 5 illustrates a block diagram of the operation of a trace material detection device in accordance with an embodiment of the disclosure.

FIG. 5 illustrates a block diagram of the operation of trace material detection device 100/300 in accordance with an embodiment of the disclosure. As shown, media 500 has been inserted through slot 104/304 in housing 102/302 and is positioned in chamber 122/322. Media 500 includes test samples 501, 502, 503, and 504 which correspond to four different materials under test that have been picked up by the user's application of media 500 against one or more surfaces of interest.

Heater 120/330 operates (e.g., in response to control signals provided by processor 112/312) to apply heat 510 to media 500 and samples 501, 502, 503, and 504 to raise their temperatures to a desired detection temperature. In some embodiments, the detection temperature may be in the range of approximately 90 degrees C. to approximately 160 degrees C., however higher or lower temperatures may be used as desired.

TABLE 1

| MATERIAL | VAPOR PRESSURE | MELTING TEMPERATURE | BOILING TEMPERATURE |
|---|---|---|---|
| sodium perchlorate | too low to measure | 468 degrees C. | 482 degrees C. |
| potassium chlorate | too low to measure | 356 degrees C. | 400 degrees C. |
| Research Department explosive (RDX) | $5 \times 10^{-7}$ Torr at 20 degrees C. | 206 degrees C. | 234 degrees C. |
| trinitrotoluene (TNT) | $2 \times 10^{-5}$ Torr at 20 degrees C. | 80 degrees C. | 240 degrees C. |
| glycerol | $2.5 \times 10^{-3}$ Torr at 50 degrees C. | 17.8 degrees C. | 290 degrees C. |
| ethanol | 45 Torr at 20 degrees C. | −114 degrees C. | 78 degrees C. |

Figure 3:
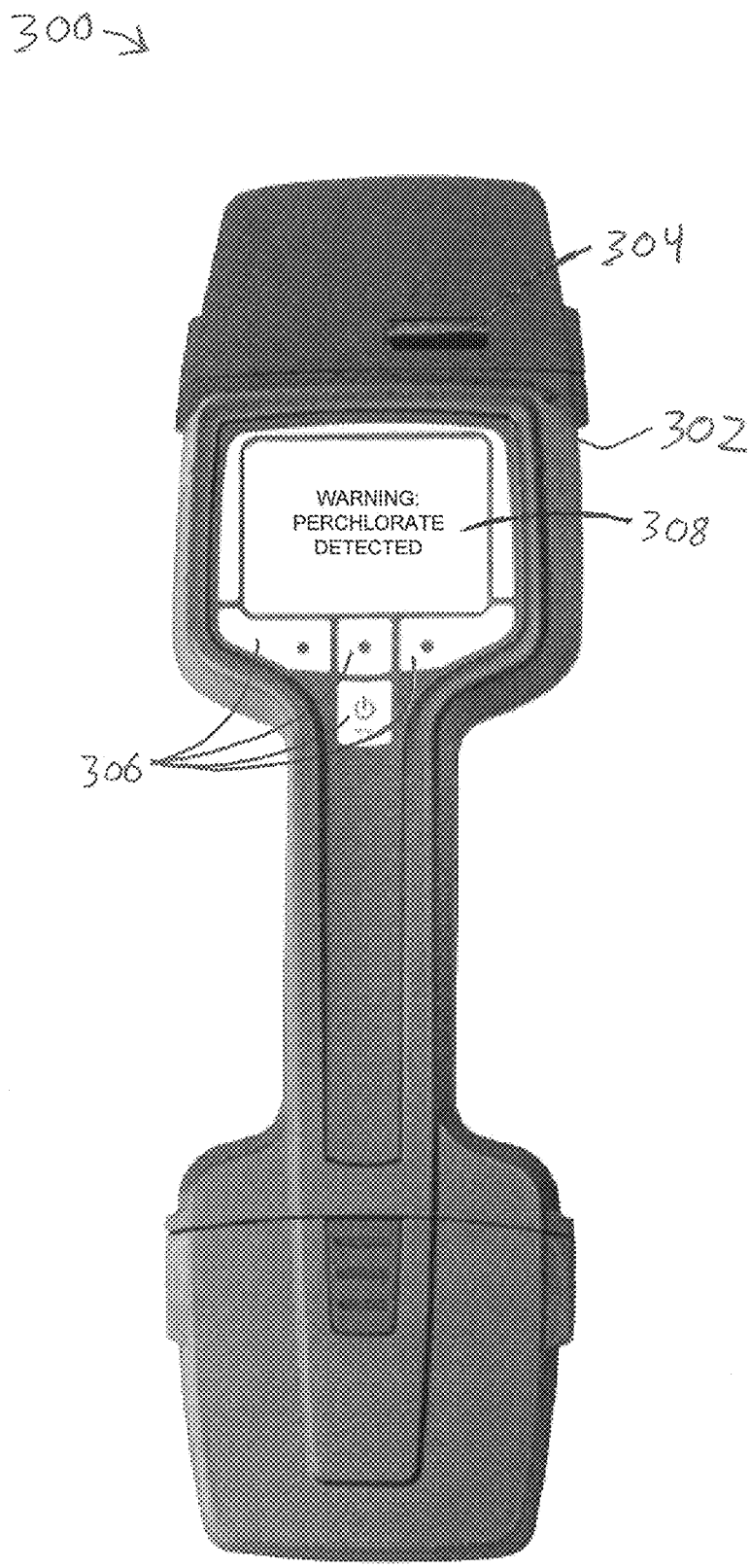
FIG. 3 illustrates an external view of a trace material detection device utilizing thermal imaging and vaporization in accordance with an embodiment of the disclosure.

FIG. 3 illustrates an external view of a trace material detection device 300 utilizing thermal imaging and vaporization in accordance with an embodiment of the disclosure. For example, device 300 may be implemented as a handheld portable detector capable of detecting explosives and/or other materials. As shown, device 300 includes a housing 302, a slot 304, user controls 306, and a display 308, all of which may be implemented in the same or similar manner as corresponding components of device 100 previously discussed. In various embodiments, additional components of device 300 (e.g., further illustrated in FIG. 4) may be distributed at physical locations internal to and/or external to housing 302.

Figure 4:
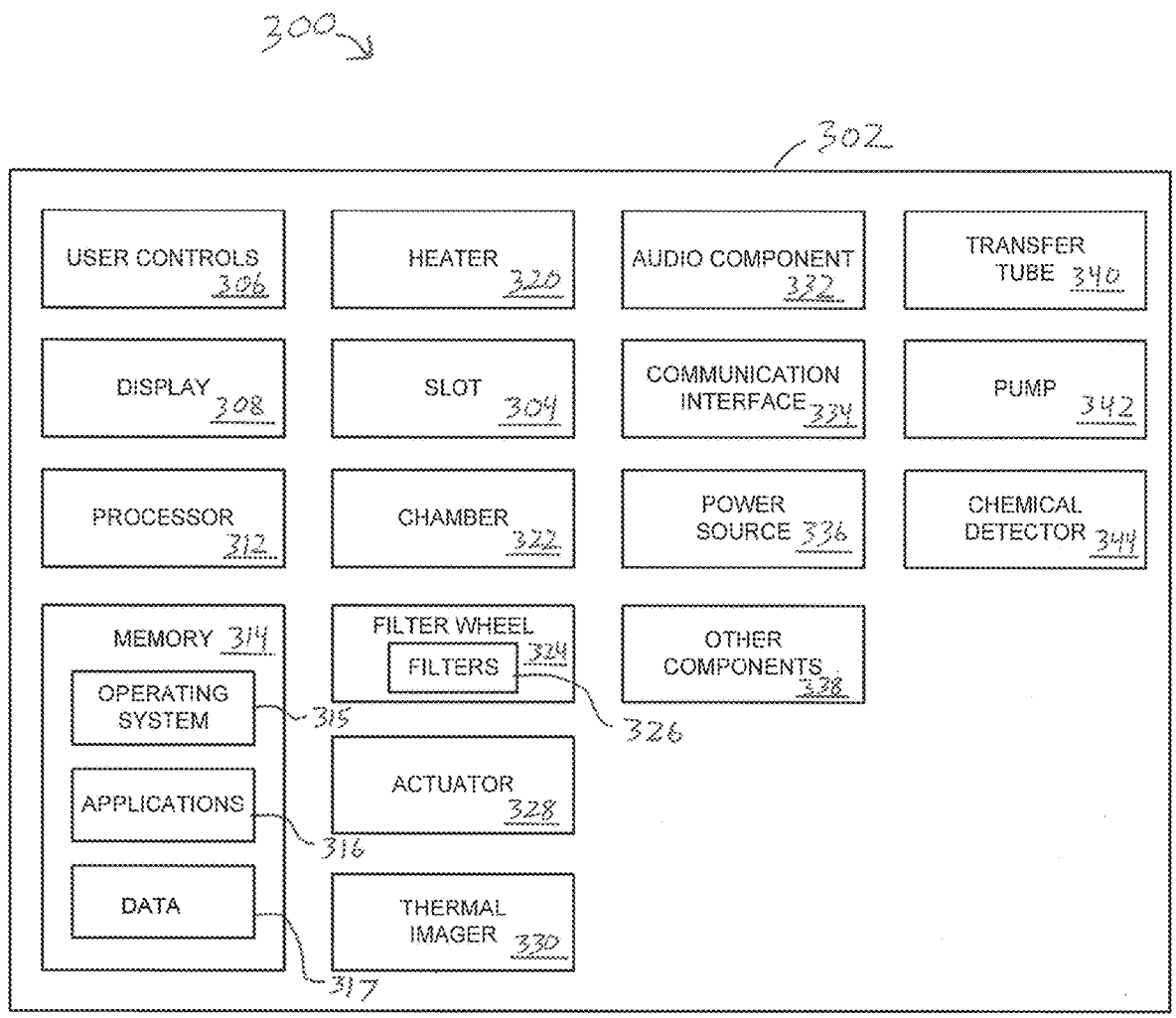
FIG. 4 illustrates a block diagram of a trace material detection device utilizing thermal imaging and vaporization in accordance with an embodiment of the disclosure.

FIG. 4 illustrates a block diagram of device 300 in accordance with an embodiment of the disclosure. In addition to several previously discussed components shown in FIG. 3, FIG. 4 further illustrates a processor 312, a memory In FIG. 5, test samples 501 and 502 are oxidizing materials that exhibit low vapor pressures. As a result, test samples 501 and 502 will remain relatively intact in response to heat 510 applied by heater 120/330 (e.g., very little of test samples 501 and 502 will vaporize). However, test samples 501 and 502 will exhibit increased amounts of thermal radiation 512 in response to heat 510. As shown, thermal radiation 512 from test samples 501 and 502 passes toward filter wheel 126/326 and thermal imager 130/330.

As discussed, filter wheel 124/324 may be rotated by actuator 128/328 to selectively position various filters 126/326 between media 500 and thermal imager 130/330. As a result, unfiltered thermal radiation 512 is received by the currently positioned filter 126/326 to provide filtered thermal radiation 514 which is received and captured by thermal imager 130/330. By positioning different filters 126/326 between media 500 and thermal imager 130/330, different filtered thermal images may be captured to provide spectral profiles for test samples 501 and 502.

As shown, filter wheel 124/324 also includes an unfiltered aperture 526 through which unfiltered thermal radiation 512 may pass to thermal imager 130/330 unchanged. As a result, thermal imager 130/330 may further capture unfiltered thermal images for use with the other filtered thermal images. For example, one or more filtered thermal images may be subtracted, added, subtracted, and/or otherwise combined with an unfiltered thermal image to generate a new thermal image corresponding to a different range of thermal radiation wavelengths.

Although a single thermal imager 130/330 is illustrated with filters 126/326 provided by filter wheel 124/324, other embodiments are contemplated. For example, in some embodiments, thermal imager 130/330 may be implemented by a plurality of image capture devices, each of which may be associated with a particular filter 126/326. In this regard, each of the image capture devices may be associated with a different corresponding one of the filters 126/326 (e.g., dedicated or otherwise). As such, the image capture devices may collectively capture a plurality of filtered images associated with different ranges of thermal radiation wavelengths.

As discussed, in the case of device 300, additional components are provided to perform vapor-phase chemical analysis. These components are further shown in FIG. 5 and discussed below in relation to test samples 503 and 504. In this regard, test samples 503 and 504 may be materials that completely or partially vaporize upon heating. In some embodiments, one or more of test samples 503 and 504 may substantially vaporize upon heating to be detected using vapor-phase chemical analysis as further discussed below. In other embodiments, one or more of test samples 503 and 504 may decompose into different components upon heating (e.g., a solid component and a gas component). In this regard, the solid component may remain on media 500 to be detected using imaging techniques as discussed, and the gas component may vaporize to be detected using vapor-phase chemical analysis as further discussed below.

As a result, test samples 503 and 504 will at least partially vaporize in response to heat 510 applied by heater 120/330 to provide analytes 520 (e.g., corresponding to vaporized portions of test samples 503 and 504). Pump 342 operates to draw analytes 520 through transfer tube 340 and into chemical detector 344. Based on interactions between analytes 520 and chemical detector 344 (e.g., performing trace detection), the presence of certain materials of interest may be determined.

Thus, it will be appreciated that the various illustrated components of devices 100 and 300 may be used to perform spectral analysis and/or vapor-phase chemical analysis as appropriate for various types of test samples. Further aspects of the operation of devices 100 and 300 are discussed below with regard to FIG. 6.

Figure 6:
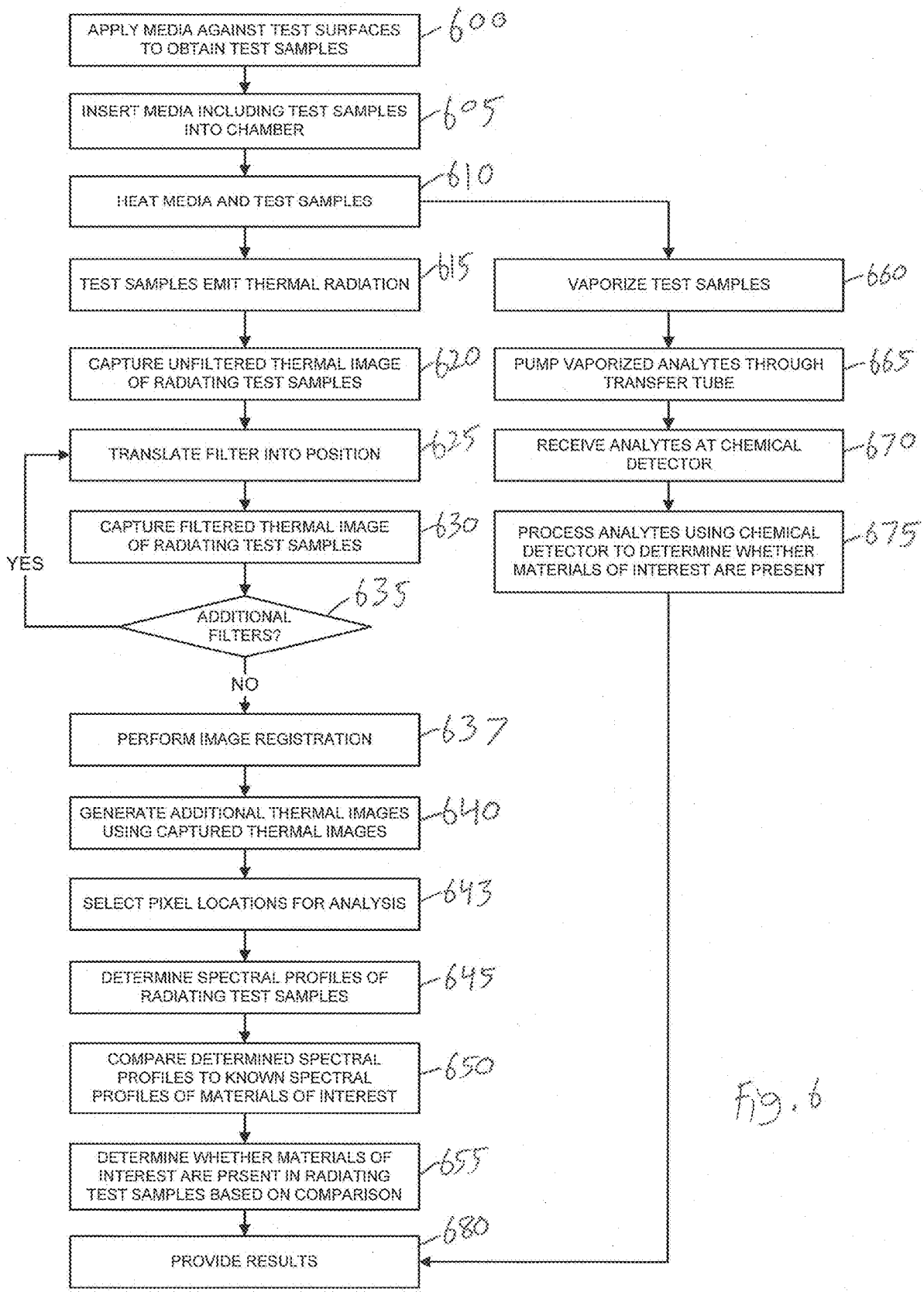
FIG. 6 illustrates a process of operating a trace material detection device in accordance with an embodiment of the disclosure.

FIG. 6 illustrates a process of operating trace material detection device 100/300 in accordance with an embodiment of the disclosure. In block 600, a user applies media 500 against a test surface (e.g., a package, luggage, clothing, or other article) to obtain one or more test samples (e.g., test samples 501, 502, 503, and 504 as shown in FIG. 5) corresponding to trace materials residing on the test surfaces.

In block 605, the user inserts media 500 through slot 104/304 and into chamber 122/322 as shown in FIG. 5. In block 610, heater 120/330 applies heat 510 to media 500 and test samples 501 and 502. In various embodiments, processor 112/312 may operate heater 120/330 in response to the user's operation of one or more user controls 106/306 and/or automatically in response to the insertion of media 500 into chamber 122/322.

Following block 610, in some embodiments, device 100/300 may perform blocks 615 to 655 to detect materials using thermal imaging techniques as discussed. Also, in some embodiments, device 300 may perform blocks 660 to 675 to detect materials using vapor-phase chemical detection techniques.

Turning first to the thermal imaging techniques, in block 615, test samples 501 and 502 (e.g., oxidizing materials) emit thermal radiation 512 in response to heat 510. In this regard, the heating operation of block 610 advantageously causes test samples 501 and 502 to emit far greater amounts of thermal radiation (e.g., greater numbers of photons) to be captured by thermal imager 130/330 than would otherwise be available at room temperature. As discussed, thermal radiation 512 passes toward filter wheel 126/326 and thermal imager 130/330.

In block 620, thermal imager 130/330 captures an unfiltered thermal image of thermal radiation 512 while unfiltered aperture 526 is positioned between media 500 and thermal imager 130/330. Accordingly, in this case, thermal radiation 512 will substantially correspond to thermal radiation 514. As discussed, this unfiltered thermal image may be selectively combined with other thermal images to generate additional thermal images as desired.

Figure 7:
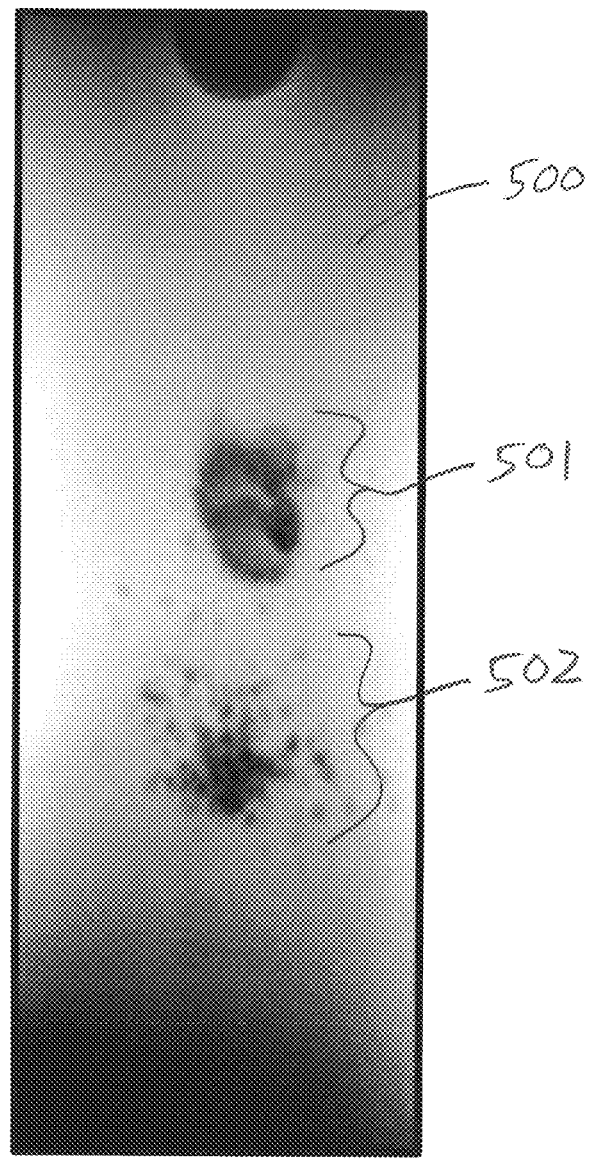
FIG. 7 illustrates an example thermal image captured by a trace material detection device in accordance with an embodiment of the disclosure.

For example, FIG. 7 illustrates an example thermal image 700 captured in block 620 in accordance with an embodiment of the disclosure. As shown, test samples 501 and 502 are both present and emitting thermal radiation in a manner that contrasts with media 500 (e.g., test samples 503 and 504 have been substantially vaporized in this example and are therefore not shown in FIG. 7). In FIG. 7, test sample 501 is potassium perchlorate and test sample 502 is sodium chloride. However, without further information, the actual chemical composition of test samples 501 and 502 may not be readily apparent to a user. By capturing additional filtered thermal images corresponding to various ranges of thermal radiation, different thermal wavelengths associated with test samples 501 and 502 may be captured. As a result, spectral profiles of test samples 501 and 502 may be determined to more specifically identify the materials present therein.

Although the capturing of unfiltered thermal images is contemplated, this is not required. For example, in some embodiments, only filtered thermal images may be desired.

Returning to FIG. 6, in block 625, actuator 128/328 operates filter wheel 124/324 to translate a desired filter 126/326 into position. Thereafter, in block 630, thermal imager 130/330 captures a filtered thermal image of the filtered thermal radiation 514.

If it is desired to apply additional filters 126/326 to capture additional filtered thermal images (block 635), then the process returns to block 625. The process of FIG. 6 may iterate through blocks 625 to 635 until a desired set of filtered thermal images are captured (e.g., corresponding to all of filters 126/326 or a subset thereof).

In some embodiments, filters 126/326 may be implemented by a set of four filters as set forth in the following Table 2 (e.g., corresponding to the four filters 126/326 illustrated in FIG. 5). Although particular filter types are identified in Table 2, it will be appreciated that any desired number of filters having any desired thermal wavelength ranges may be used in various embodiments.

TABLE 2

EXAMPLE FILTERS 11.55 µm longpass
8 µm to 11 µm bandpass
9.7 µm shortpass
8.7 µm shortpass Thus, after all filters 126/326 in this example have been used, thermal imager 130/330 will have captured at least five thermal images, namely: an unfiltered thermal image, a 11.55 µm longpass filtered thermal image, an 8 µm to 11 µm bandpass filtered thermal image, a 9.7 µm shortpass filtered thermal image, and a 8.7 µm shortpass filtered thermal image. Other types and numbers of filters are contemplated, for example, as further discussed herein with regard to Table 5.

In block 637, processor 112/312 may perform one or more thermal image registration operations. Such operations may align the various thermal images relative to each other before further processing to thus compensate for the various unintended misalignment artifacts as further discussed herein with regard to FIGS. 19-21. In some embodiments, one or more visible light imagers may be used to capture visible light images of media 500 to be used as reference images to perform image registration of the thermal images.

In block 640, processor 112/312 operates to generate one or more additional thermal images based on the thermal images previously captured in blocks 620 and 630. As discussed, additional thermal images having additional different ranges may be generated by selectively subtracting, adding, and/or otherwise combining the previously captured thermal images in order to maximize the distinction between the material of interest and the media or other benign components. For example, the following Table 3 identifies six example thermal images that may be provided using various combinations of the previously captured thermal images.

TABLE 3

| THERMAL IMAGE/BIN | THERMAL RADIATION WAVELENGTH RANGES | COMBINATIONS OF THERMAL IMAGES USED TO GENERATE |
|---|---|---|
| 1 | 11.55 µm longpass | 11.55 µm longpass |
| 2 | 9.7 µm to 11.55 µm bandpass | Unfiltered SUBTRACT 9.7 µm shortpass SUBTRACT 11.55 µm longpass |
| 3 | 8.7 µm to 9.7 µm bandpass | 9.7 µm shortpass SUBTRACT 8.7 µm shortpass |
| 4 | 8.7 µm shortpass | 8.7 µm shortpass |
| 5 | 11 µm to 11.55 µm bandpass AND 8 µm shortpass | Unfiltered thermal image SUBTRACT 11.55 µm longpass SUBTRACT 8 µm to 11 µm bandpass |
| 6 | 9.7 µm to 11 µm bandpass AND 8 µm to 8.7 µm bandpass | 8 µm to 11 µm bandpass ADD 8.7 µm shortpass SUBTRACT 9.7 µm shortpass |

As set forth in Table 3, thermal image 1 is provided by the original filtered thermal image captured using a 11.55 µm longpass filter. The remaining thermal images 2 to 6 are generated by adding and/or subtracting various combinations of filtered and unfiltered thermal images. Thus, as identified in Table 3, thermal images having a variety of different thermal radiation wavelength ranges may be obtained from a relatively small set of filters 126/326 (e.g., four filters).

Although the generating of additional thermal images through combining various captured thermal images can be used in certain embodiments, this is not required. For example, in some embodiments, the captured thermal images themselves may be sufficient to determine spectral profiles and identify materials as desired.

In block 643, processor 112/312 selects one or more pixel locations of the captured and/or generated thermal images for which to determine spectral profiles associated with test samples 501 and 502. In some embodiments, one or more individual pixel locations of the thermal images corresponding to test samples 501 and 502 may be selected. For example, spectral profiles associated with the individual pixel locations may be used as representative of test samples 501 and 502. In other embodiments, additional pixel locations or all pixel locations of the thermal images may be selected. In such cases, spectral profiles may be determined and corresponding analysis may be performed for many pixel locations of the thermal images, thus providing pixel-wise determinations for materials that may be present throughout the thermal images. In yet other embodiments, spectral profiles may be determined based on the overall thermal radiation for a particular wavelength range as distributed over a corresponding thermal image as a whole. Additional examples of the use of various pixel locations is further discussed with regard to FIGS. 13-14.

In block 645, processor 112/312 operates on the captured and/or generated thermal images to determine a spectral profile associated with test samples 501 and 502. For example, in some embodiments, processor 112/312 may perform a statistical analysis on the captured thermal images to determine a set of values corresponding to the intensity of thermal radiation represented in the selected pixel locations of the thermal images corresponding to the various wavelength ranges.

Considering the thermal images identified in Table 3 above, processor 112/312 may determine a value for each thermal image corresponding to a normalized intensity value of the thermal radiation captured in the image (e.g., based on the detected values or "counts" of corresponding infrared sensors of thermal imager 130/330). Because each thermal image corresponds to a different range of wavelengths, this set of spectral profile values represents the relative contributions of different ranges of thermal radiation emitted by test samples 501 and 502. The different wavelength ranges are also referred to as "bins," each of which may have an associated normalized count value. Accordingly, the spectral profile based on thermal images of Table 3 may be represented as a set of six bin values.

In block 650, processor 112/312 compares the determined spectral profile to a set of known spectral profiles associated with various materials of interest. In some embodiments, the spectral profiles may be may be stored as a library of spectral profiles in data 117/317 which may be generated a priori by acquiring spectra of known materials, also referred to as training data. For example, FIGS. 8-11 illustrate various known spectral profiles in accordance with embodiments of the disclosure. In each of FIGS. 8-11, normalized intensity values are identified for each of six bins corresponding to thermal images/bins 1-6 of Table 3 for a variety of different materials. As shown, different materials exhibit different spectral profiles, while families of similar materials (e.g., perchlorate, chlorate, and nitrate families) exhibit similar spectral profiles.

Figure 8:
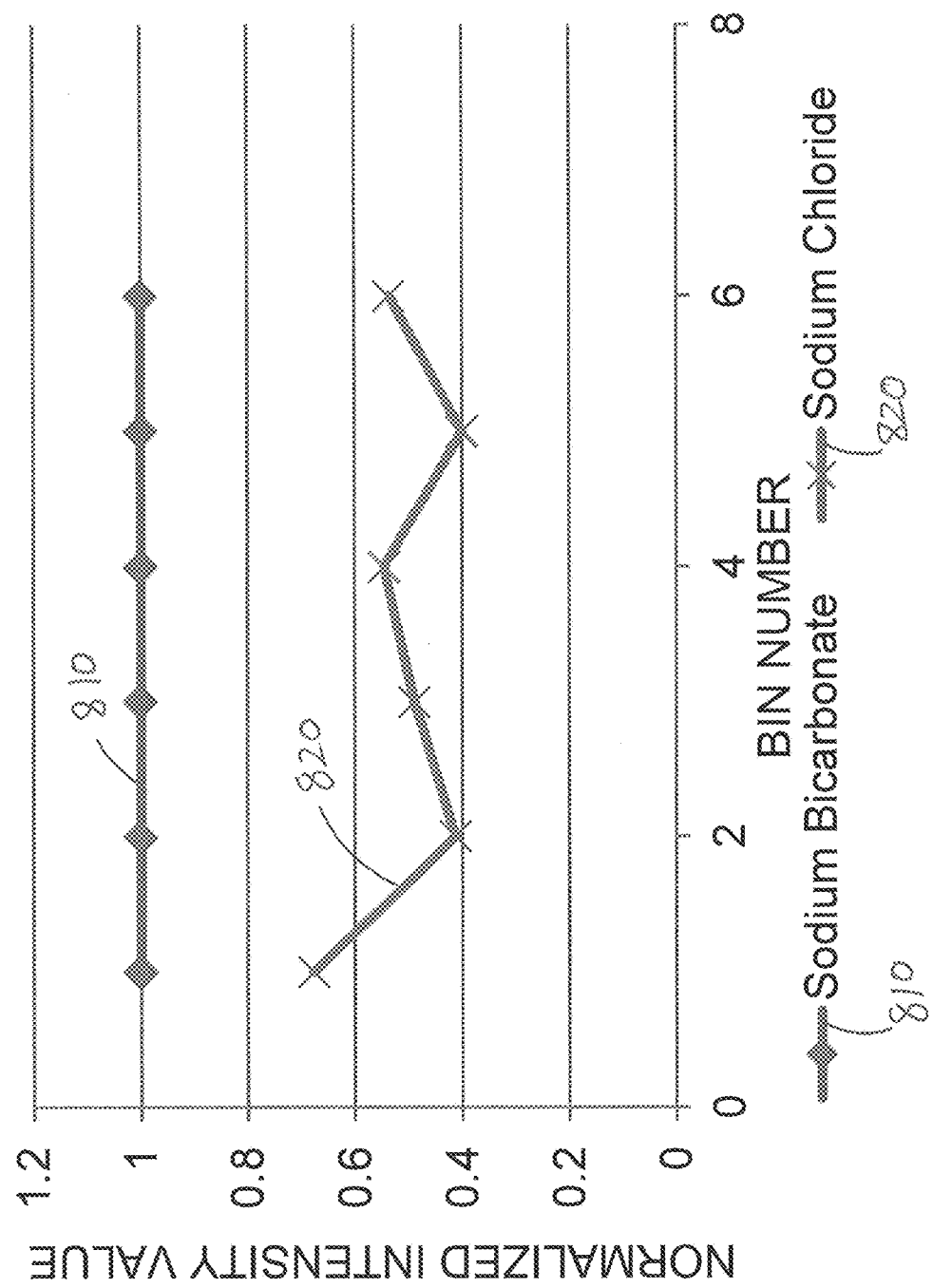
FIGS. 8-11 illustrate various spectral profiles in accordance with embodiments of the disclosure.
Figure 9:
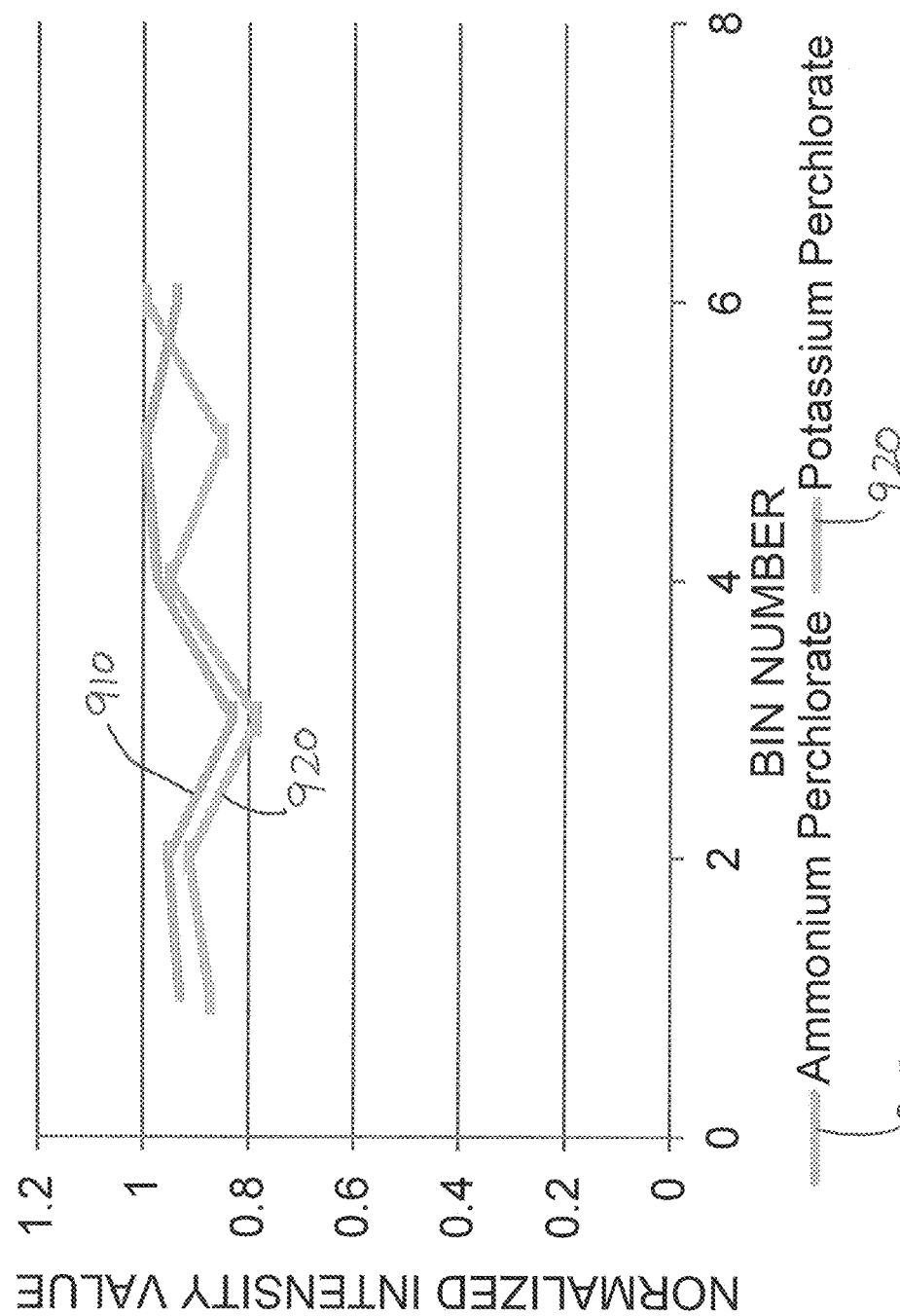

In FIG. 8, the spectral profiles of several reference salts are provided, with sodium bicarbonate 810 having a relatively uniform spectral profile, and sodium chloride 820 exhibiting a much different spectral profile. In FIG. 9, the spectral profiles of several perchlorates are provided, with ammonium perchlorate 910 and potassium perchlorate 920 exhibiting similar spectral profiles that are characteristic of perchlorates.

Figure 10:
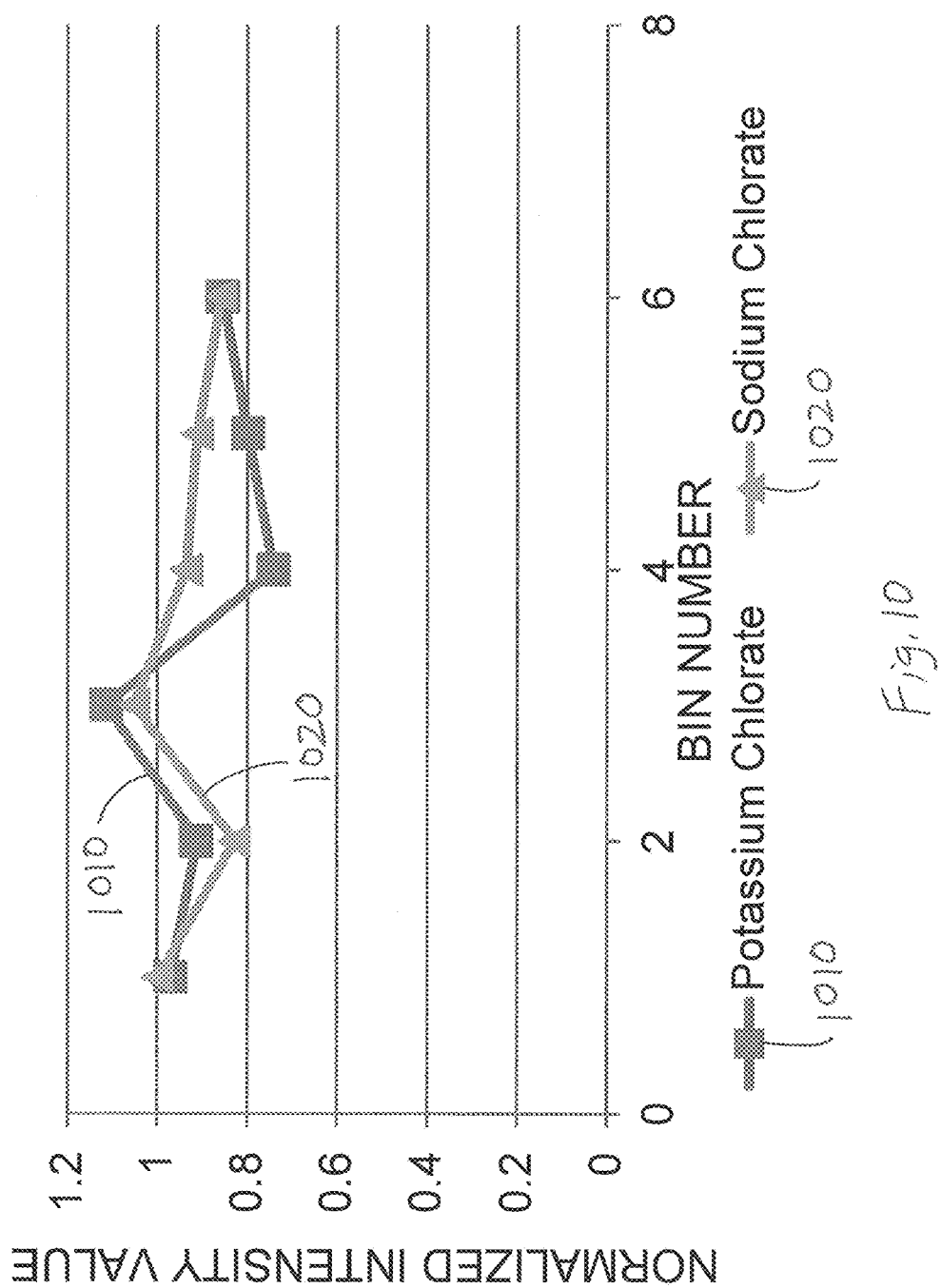
Figure 11:
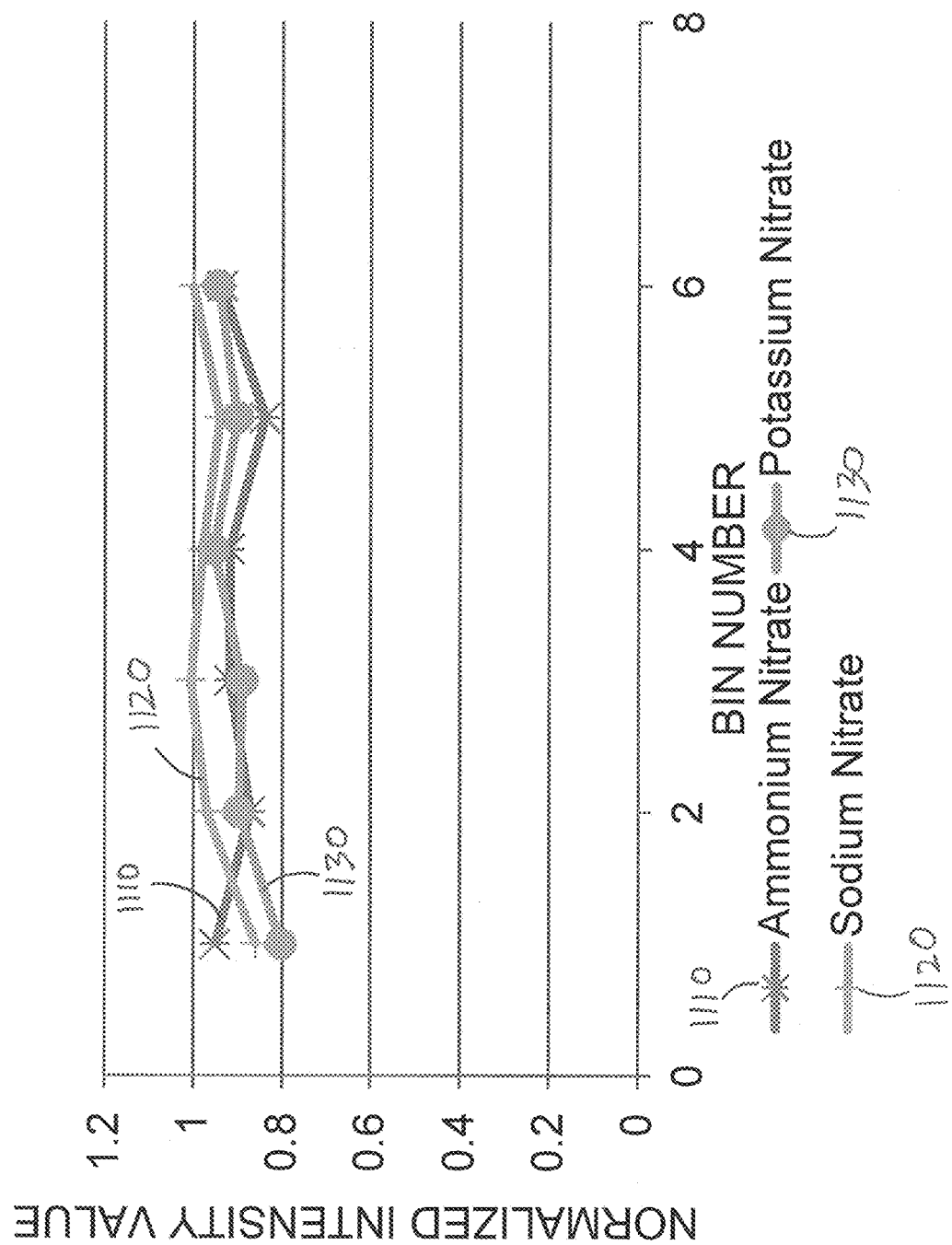

In FIG. 10, the spectral profiles of several chlorates are provided, with potassium chlorate 1010 and sodium chlorate 1020 exhibiting similar spectral profiles that are characteristic of chlorates. In FIG. 11, the spectral profiles of several nitrates are provided, with ammonium nitrate 1110, potassium nitrate 1130, and sodium nitrate 1120 exhibiting similar spectral profiles that are characteristic of nitrates.

Thus, by comparing one or more spectral profiles (previously determined in block 645) with various spectral profiles shown in FIGS. 8-10, processor 112/312 may rapidly and efficiently determine whether test samples 501 and 502 belong to a particular family of materials (e.g., salts including perchlorates, chlorates, nitrates, and/or others). Even if the particular material in a family is not explicitly identified by the comparison, a determination of the overall family is highly beneficial to conclude whether materials of interest are present on the test surface. Accordingly, in block 655, processor 112/312 determines whether materials of interest are present in test samples 501 or 502 based on the results of the spectral profile comparison.

The vapor-phase chemical detection process of blocks 660 to 675 will now be discussed. In various embodiments, blocks 660 to 675 may be performed simultaneously and/or sequentially with blocks 615 to 655.

In block 660, test samples 503 and 504 are at least partially vaporized to provide analytes 520 in response to heat 510 applied by heater 120/330. In block 665, pump 342 operates to draw analytes 520 through transfer tube 340. In block 670, analytes 520 are received by chemical detector 344. In block 675, chemical detector 344 processes analytes 520 to determine whether materials of interest are present. For example, in some embodiments, chemical detector 344 may monitor the response of fluorescent polymers to analytes 520 to perform this determination.

In block 680, the results of blocks 655 and 675 are provided to the user, for example, by messages and/or graphics provided by display 108/308, audible notifications provided by audio component 132/332, and/or other techniques as appropriate.

In view of the present disclosure, it will be appreciated that various materials of interest may be detected using thermal imaging techniques and/or vapor-phase chemical detection techniques. As a result, appropriate devices and methods may be deployed in a flexible and convenient manner to identify the presence of materials in a low cost, rapid, and highly portable manner that is particularly effective when detection is needed in the field.

Although particular wavelength ranges have been identified for filters 126/326 and the various captured and generated thermal images in Tables 1 and 2 discussed above, other numbers and types of filters and different wavelength ranges may be used to detect additional materials. For example, the following Table 4 identifies a non-exhaustive list of various example materials that may be detected using thermal imaging techniques through the use of appropriate filters and wavelength ranges. As previously discussed, other filters and wavelength ranges are also contemplated:

TABLE 4

| EXAMPLE MATERIALS | |
|---|---|
| sodium bicarbonate | potassium permanganate |
| sodium chloride | other volatile and non-volatile permanganates |
| ammonium perchlorate | other volatile and non-volatile dichromates |
| potassium perchlorate | Research Department explosive (RDX) |
| sodium perchlorate | trinitrotoluene (TNT) |
| other volatile and non-volatile perchlorates | pentaerythritol tetranitrate (PETN) |
| potassium chlorate | other explosive materials |
| sodium chlorate | cocaine |
| other volatile and non-volatile chlorates | heroin |
| ammonium nitrate | amphetamine |
| potassium nitrate | methamphetamine |
| sodium nitrate | 3,4-methylenedioxymethamphetamine (MDMA) |
| urea nitrate | other narcotics |
| other volatile and non-volatile nitrates | other volatile and non-volatile materials |

Various principles of the present disclosure will now be discussed particularly in relation to example embodiments wherein infrared sensors of thermal imager 130/330 are implemented with microbolometers. However, it will be understood that other embodiments including non-microbolometer implementations for infrared sensors are also contemplated.

As discussed, any desired number of filters 126/326 having any desired thermal wavelength ranges may be used in various embodiments. The following Table 5 illustrates six example filters that may be used to implement filters 126/326 in some embodiments:

TABLE 5

| FILTER NUMBER | FILTER TYPE | CENTER/STOPBAND WAVELENGTH | BANDWIDTH |
|---|---|---|---|
| 1220 | shortpass | 8.85 µm | shortpass |
| 1230 | bandpass | 8.95 µm | 330 nm |
| 1240 | bandpass | 9.48 µm | 613 nm |
| 1250 | bandpass | 10.35 µm | 460 nm |
| 1260 | bandpass | 10.6 µm | 1500 nm |
| 1270 | longpass | 11.0 µm | longpass |

Figure 12:
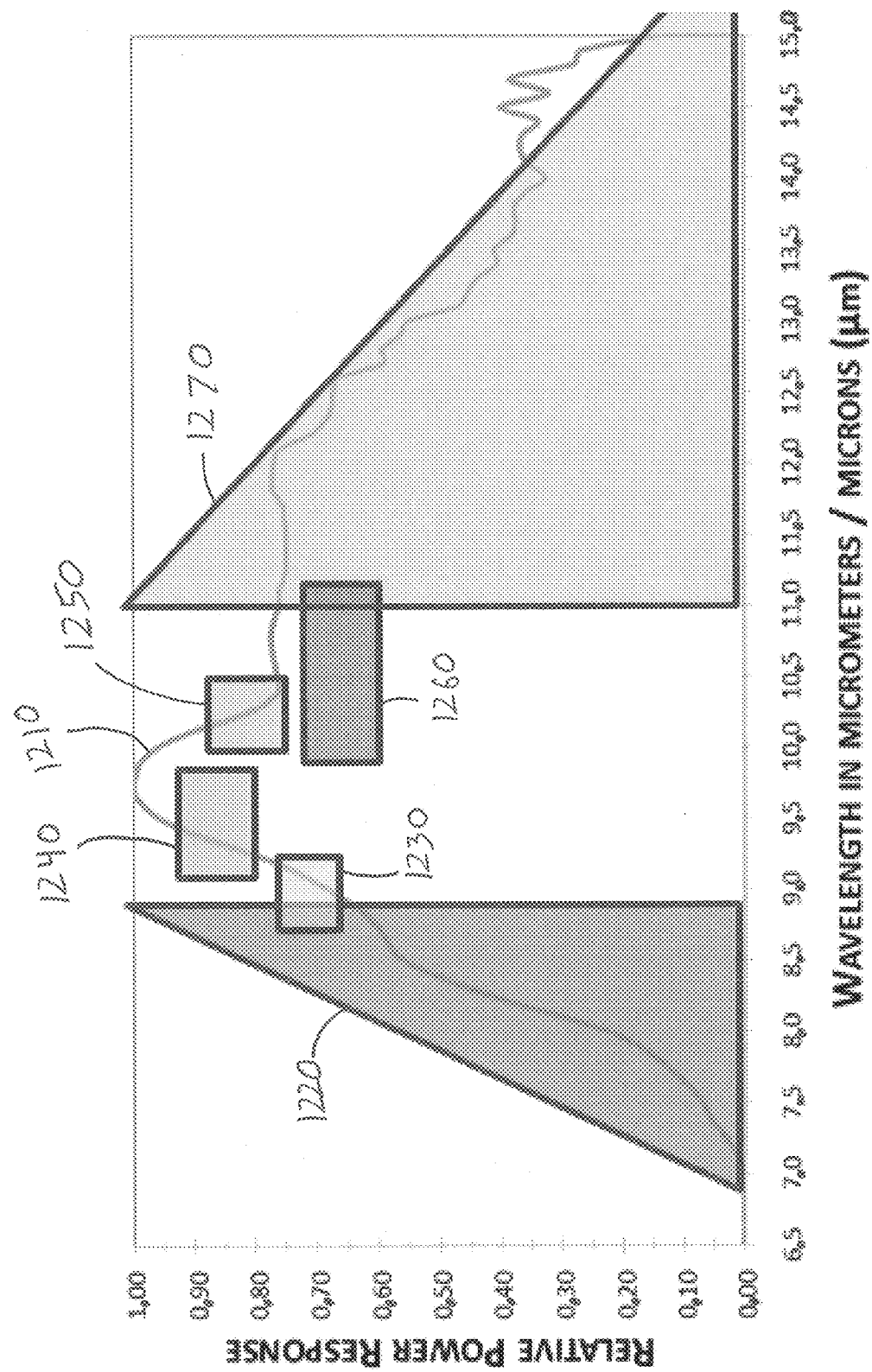
FIG. 12 illustrates a microbolometer spectral sensitivity plot and associated wavelengths of several filters in accordance with an embodiment of the disclosure.

FIG. 12 illustrates a microbolometer spectral sensitivity plot 1210 and associated wavelengths of several filters 1220 to 1270 in accordance with an embodiment of the disclosure. As shown by plot 1210, the microbolometers of thermal imager 130/330 have a spectral sensitivity that varies with wavelength, resulting in a corresponding variation in relative power response.

For example, plot 1210 identifies an imager-specific spectral sensitivity that is useful for thermal images captured over wavelength range of approximately 7 μm to approximately 14 μm. As shown, the spectral sensitivity peaks at approximately 9.7 μm and tapers off above and below that point. In particular, a band of relatively high responsivity (e.g., from approximately 8.75 μm to approximately 12.25 μm) is bordered by bands of significantly lower responsivity (e.g., from approximately 7.0 μm to approximately 8.75 μm and from approximately 12.25 μm to approximately 15 μm).

Although plot 1210 applies to a specific microbolometer implementation, other types of imagers may exhibit different spectral sensitivity plots. For example, mercury cadmium telluride (MCT) imagers or strained layer superlattice (SLS) imagers may be associated with different plots. Also, in some embodiments, individual detectors of an imager may have different sensitivities. For example, in some cases, individual microbolometers may themselves exhibit different spectral sensitivity plots.

The type and bandwidth of filters 1220 to 1270 may be selected such that their photon throughput results in comparable pixel values (e.g., preferably of the same order of magnitude) being provided by microbolometers for thermal images captured with different filters in place. For example, filter 1220 is a shortpass filter with a stopband wavelength at 8.85 μm to accommodate a rising sensitivity exhibited by plot 1210 over its range. Filter 1270 is a longpass filter with a stopband wavelength at 11.0 μm to accommodate a falling sensitivity exhibited by plot 1210 over its range. Additional filters 1230, 1240, 1250, and 1260 are bandpass filters with significantly smaller bandwidths to accommodate the higher sensitivity exhibited by plot 1210 over their respective ranges.

Figure 13:
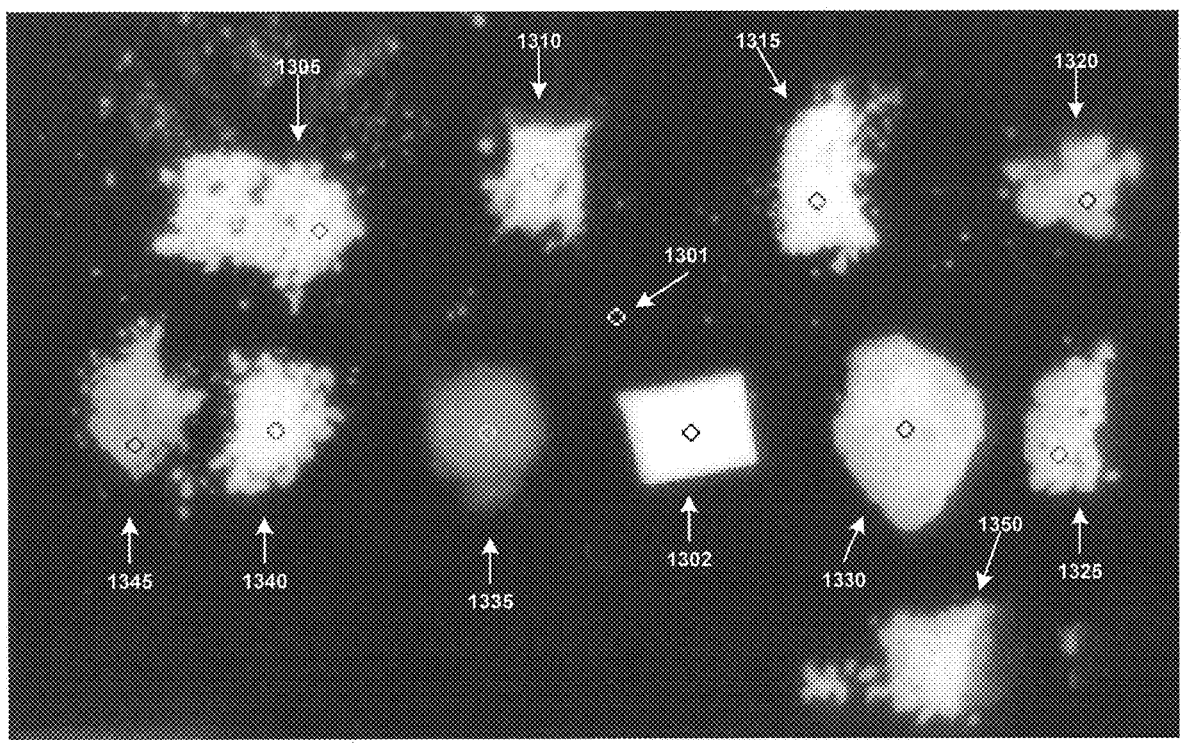
FIG. 13 illustrates a thermal image of a plurality of materials in accordance with an embodiment of the disclosure.

FIG. 13 illustrates a thermal image 1300 captured of a plurality of materials in accordance with an embodiment of the disclosure. The example thermal image 1300 was captured of a scene by a thermal imager (e.g., thermal imager 130/330) while filter 1240 was applied. In this example, the captured scene includes a variety of materials 1305 to 1345, a mixture 1350 of materials, and additional material 1302, all provided on a substrate 1301 to illustrate various principles of the present disclosure. In various embodiments, any of these and/or other materials may be provided on media 500 and imaged by thermal imager 130/330 as previously discussed.

In thermal image 1300, a single pixel location is identified (e.g., circled) for each of materials 1305 to 1345, substrate 1301, and material 1302. Values of these identified pixel locations for various thermal image frames are further discussed herein with regard to FIG. 14. As discussed, such pixel locations may be selected by processor 112/312 in block 643 of FIG. 6.

Figure 14:
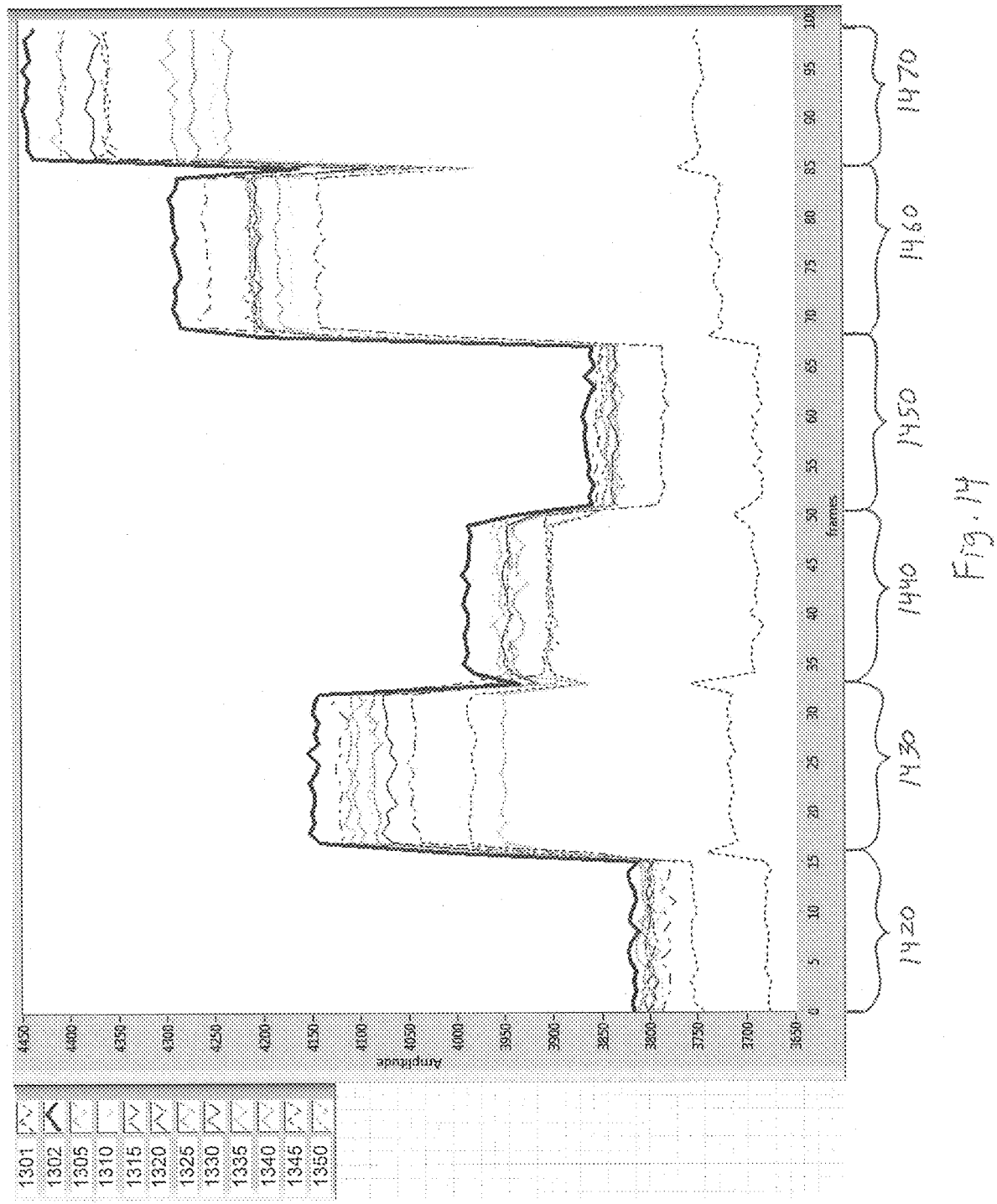
FIG. 14 illustrates plots of pixel values taken from filtered thermal images of the materials of FIG. 13 in accordance with an embodiment of the disclosure.

FIG. 14 illustrates plots of pixel values associated with the pixel locations identified in FIG. 13 taken from a plurality of filtered thermal images in accordance with an embodiment of the disclosure. In this regard, approximately one hundred thermal images (e.g., image frames) were captured of the scene illustrated in FIG. 13, and the respective pixel values associated with the identified pixel locations are shown for each thermal image.

As shown in FIG. 14, each of filters 1420 to 1470 were separately applied to the scene (e.g., filters 1420 to 1470 were individually positioned between the scene and imager 130/330 during block 625 while the thermal images were captured in block 630). Sets of thermal images (e.g., approximately 16 thermal images) were captured for each filter, and approximately one thermal image was captured during the switching of each filter. For example, frames 0 to 15 were captured while filter 1420 was applied, frame 16 was captured while filter 1420 was switched to filter 1430 (e.g., by rotation of filter wheel 124/324, frames 17 to 32 were captured while filter 1430 was applied, and so on.

As also shown in FIG. 14, the pixel values for the various materials remain relatively consistent for thermal images captured with the same filter (e.g., the plots appear substantially flat with only minor variations while a particular filter is applied). By averaging the pixel values of image frames associated with a particular material and a particular filter, an average pixel value may be determined for each material when a specific filter is applied. For example, in the case of material 1335, average values of approximately 3810, 3945, 3950, 3840, 4210, and 4280 may be determined for filters 1420, 1430, 1440, 1450, 1460, and 1470, respectively.

Such averaging may be performed, for example, by processor 112/312 in block 645 of FIG. 6. The average pixel values determined for each material correspond to a spectral profile for the material that may be compared to known spectral profiles to identify the material, for example, by processor 112/312 in block 650 of FIG. 6

In some embodiments, calibrated emissivity values may be used for such comparisons rather than direct pixel values. This calibration may be performed, for example, using materials with known emissivity values. For example, substrate 1301 may be a known aluminum substrate having a relatively low emissivity (e.g., approximately 0.07 in the LWIR band). Accordingly, the plot in FIG. 14 associated with substrate 1301 exhibits the lowest pixel values detected by thermal imager 130/330 for all applied filters.

Also in this example, material 1302 is a known black material having a relatively high emissivity (e.g., approximately 1 in the LWIR band). Therefore, the plot in FIG. 14 associated with material 1350 exhibits the highest pixel values detected by thermal imager 130/330 for all applied filters.

Thus, substrate 1301 and material 1302 provide approximate lower and upper bounds, respectively, for the pixel values of other materials 1305 to 1345 shown in FIG. 14 and can be used to calibrate the emissivity of those other materials. In this regard, the pixel values of substrate 1301 and material 1302 effectively correspond to the dynamic range of the pixel values expected for all imaged materials. Moreover, since the pixel values of substrate 1301 and material 1302 generally correspond to emissivities of approximately 0.07 and approximately 1, their pixel values may also be used to determine emissivities of other materials based on associated pixel values.

For example, in the following equation, It is an average pixel value associated with one of filters 1420 to 1470 for of one of materials 1305 to 1345 to be calibrated, Ir0 is a pixel value of substrate 1301, and Ir1 is a pixel value of black material 1302:

$$em = \frac{I_t - I_{r0}}{I_{r1} - I_{r0}}$$

Accordingly, an emissivity value for each combination of materials 1305 to 1345 and filters 1420 to 1470 may be determined and used to provide a spectral profile for each material (e.g., in block 645 of FIG. 6). Such emissivity values may be used as the spectral profile to be compared with other known spectral profiles to identify materials 1305 to 1345 (e.g., in block 650 of FIG. 6).

Although filters 1420 to 1470 have been discussed with regard to processing pixel values associated with a single pixel location, additional pixels may be processed. For example, in some embodiments, a spectral profile may be determined for each pixel location of the captured thermal images. Although such approaches may entail considerable processing resources (e.g., a spectral profile is determined for pixel values corresponding to every pixel location of the images rather than only one representative pixel for each material), this approach permits pixel-wise determinations of materials as further discussed herein.

In some embodiments, processor 112/312 may perform one or more machine learning processes in block 650 to identify materials 1305 to 1345. For example, block 650 may include the application of one or more machine learning processes to the spectral profiles determined in block 645.

In some embodiments, the machine learning processing may include performing a linear discriminant analysis (LDA) process to improve the separation the various spectral profiles associated with different materials 1305 to 1345 in a transformed feature space. Following transformation, a K-nearest neighbor (KNN) process and/or a support vector machine (SVM) process may be performed to identify a particular material following the processing of a training data set of known spectral profiles (e.g., stored in data 117/317 as discussed).

Figure 15:
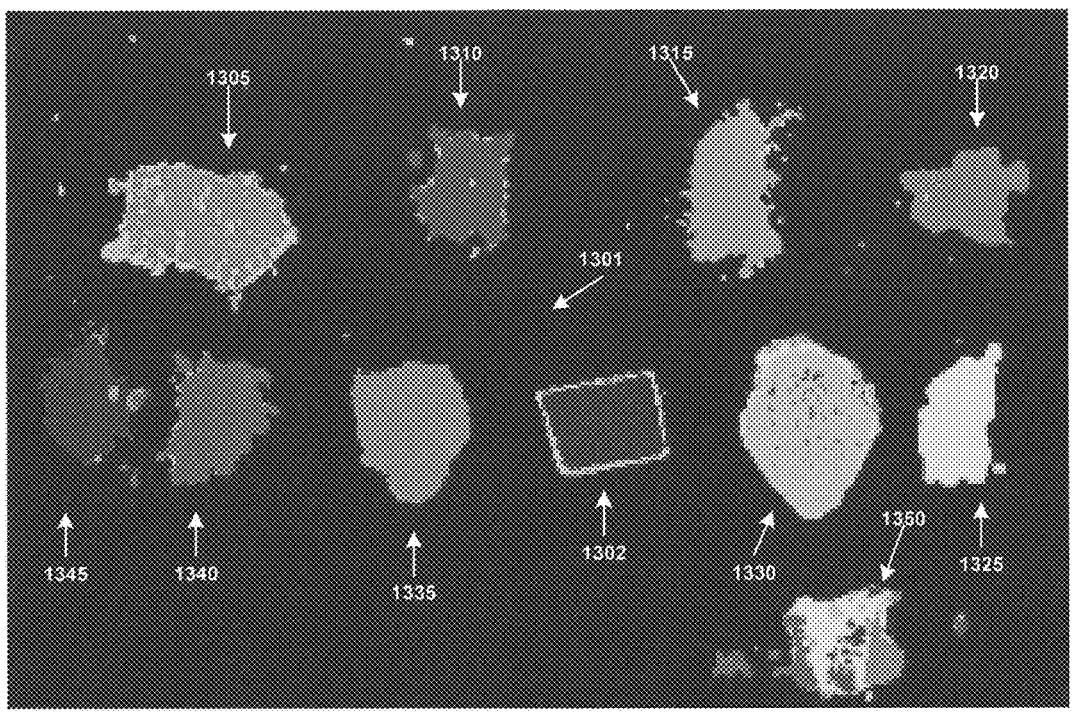
FIG. 15 illustrates a thermal image of the materials of FIG. 13 illustrating the results of machine learning processing in accordance with an embodiment of the disclosure.

FIG. 15 illustrates a thermal image 1500 of the materials of FIG. 13 illustrating the results of machine learning processing in accordance with an embodiment of the disclosure. Thermal image 1500 may be provided, for example, as part of the results in block 680. In this case, spectral profiles have been determined for all pixels of the captured thermal images (e.g., average pixel values corresponding to each of filters 1420 to 1470 have been determined for every pixel location of the images).

For example, in processed thermal image 1500, different colors are associated with different materials. Accordingly, each pixel has been colored to correspond to its particular determined material. As shown, materials 1305 to 1345 are substantially uniform, corresponding to consistent identification for each group of materials. Substrate 1301 and black material 1302 are also consistently identified. In addition, the mixture of materials 1350 is represented by multiple colors which correspond to the different materials at that location.

In some embodiments, the machine learning processing may include performing a principal component analysis (PCA) process on a determined spectral profile to identify the three filters (e.g., three selected from filters 1420 to 1470) having the most distinct pixel values or emissivities which may be respectively mapped to red, blue, and green colors of an RGB representation.

Figure 16:
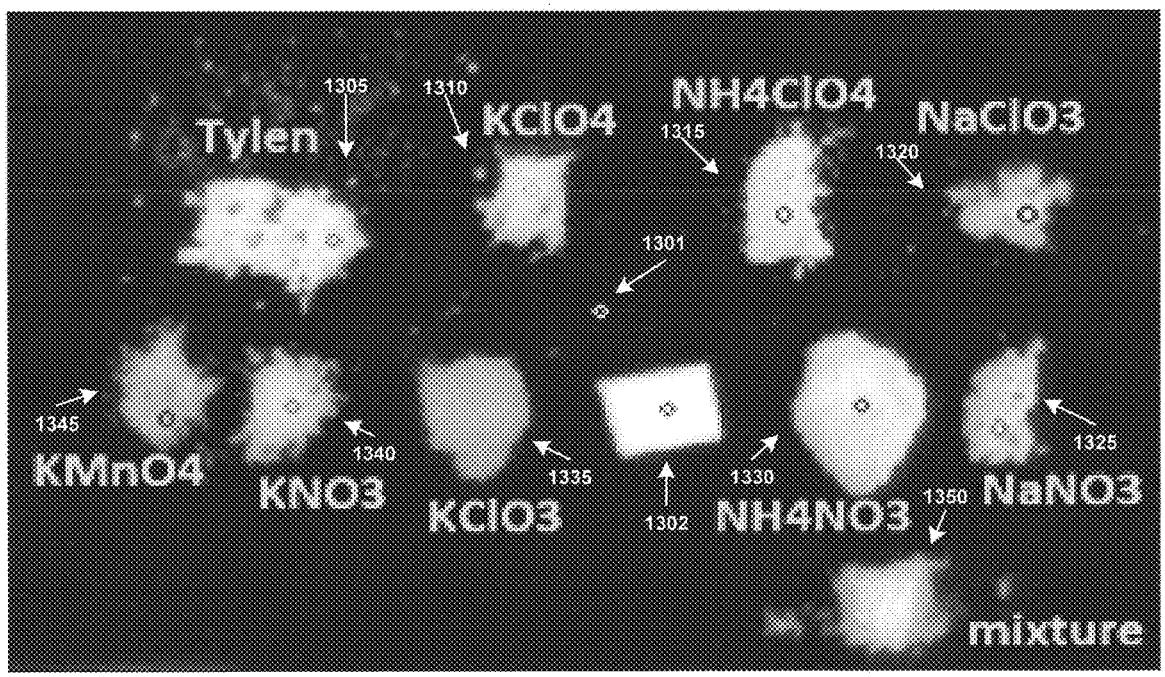
FIG. 16 illustrates a thermal image of the materials of FIG. 13 using an RGB representation in accordance with an embodiment of the disclosure.

FIG. 16 illustrates a thermal image 1600 of the materials of FIG. 13 using an RGB representation resulting from a PCA process performed for all pixels of the captured thermal images in accordance with an embodiment of the disclosure. Thermal image 1600 may be provided, for example, as part of the results in block 680. In FIG. 16, red, blue, and green intensities have been mapped to the pixel values and/or emissivities associated with filters 1430, 1460, and 1470. Also in FIG. 16, the determinations made in block 650 are superimposed thereon for reference.

Referring again to FIG. 14, it will be appreciated that the overall dynamic range of expected pixel values for each filter is relatively narrow. Indeed, many plots of FIG. 14 are within 200 counts or less of each other. Accordingly, the presence of significant noise (e.g., caused by temperature drifts associated with thermal imager 130/330 and/or other factors) may result in pixel values (or emissivity values) that may be difficult to correlate to known spectral profiles.

Accordingly, in some embodiments, thermal imager 130/330 may be implemented with various techniques to reduce temperature variations, increase dynamic range, and/or reduce noise during the capture operations of blocks 620 and 630. For example, in some embodiments, the dynamic range of thermal imager 130/330 may be increased over that of conventional imagers to permit additional photon detection by using various improvements such as, for example, fast optics (e.g., a lens having a small f-number such as f/1.1), increased integration time (e.g., increased by approximately 200% compared to conventional thermal imagers), and/or temperature stabilization.

Regarding temperature stabilization, in some embodiments, thermal imager 130/330 may be implemented as a temperature controlled thermal imager (e.g., with a thermal electric cooler or other appropriate equipment provided as part of thermal imager 130/330 and/or other components 138/338). Such temperature control can reduce long term drift and fluctuation.

For example, by maintaining thermal imager 130/330 at a temperature slightly lower than ambient temperature (e.g., approximately 3 degrees C. to approximately 5 degrees C. lower than ambient temperature, and with a stability of approximately +/−0.1 degrees C.), pixel values may be acquired with more consistent values.

Figure 17:
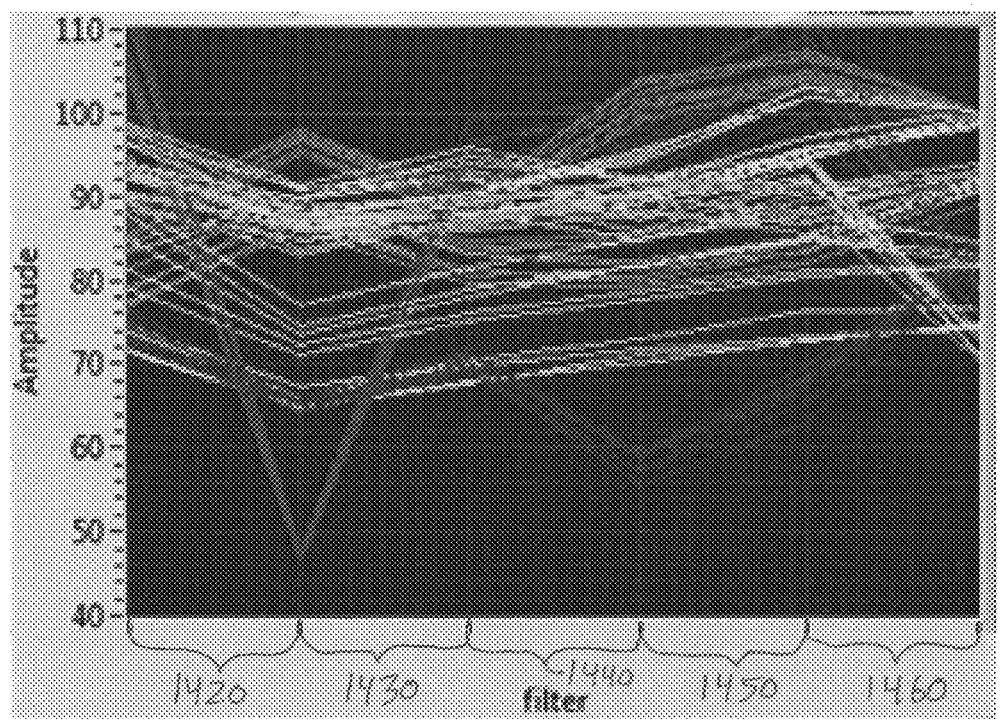
FIG. 17 illustrates plots of pixel values captured by a thermal imager without temperature stabilization in accordance with an embodiment of the disclosure.
Figure 18:
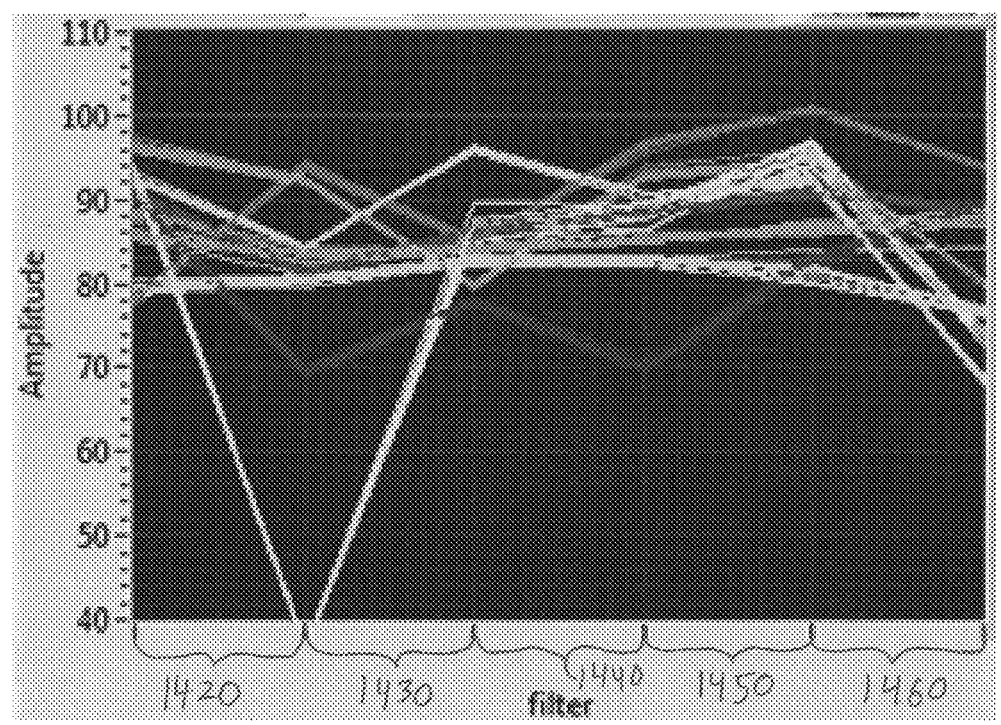
FIG. 18 illustrates plots of pixel values captured by a thermal imager with temperature stabilization in accordance with an embodiment of the disclosure.

In this regard, FIG. 17 illustrates plots of pixel values repeatedly captured by a thermal imager 130/330 using various filters, and FIG. 18 illustrates the same while using faster optics, increased integration time, and temperature stabilization as discussed above. As shown, the pixel values of FIG. 18 obtained using the various improvements discussed above are significantly more consistent than those of FIG. 17 for repeated image capture operations. Accordingly, applying such techniques can provide more consistent spectral profiles for comparison, thus improving the accuracy of material identification.

As previously discussed with regard to FIG. 5, various filters 124/324 (e.g., including any of filters 1420 to 1470 or others) may be selectively positioned in front of thermal imager 130/330 and an imaged scene (e.g., media 500 disposed in slot 104/304). In some cases, this can result in unintended misalignment of thermal images captured by different filters. For example, in some cases, the thermal images may exhibit minor optical distortion artifacts caused by misalignments of filters 124/324 relative to the thermal imager 130/330, vibrations associated with rotation of filter wheel 124/324, and/or other factors. Such misalignments may result in different pixel locations being erroneously considered together as part of the same spectral profile (e.g., pixel values associated with different pixel locations may be improperly associated with each other).

Accordingly, as discussed with regard to block 637 of FIG. 6, an image registration process may be performed on some or all of the thermal images to align them relative to each other and thus compensate for the various unintended misalignment artifacts noted above. For example, FIG. 19 illustrates a composite thermal image 1900 provided by combining a plurality of filtered thermal images without performing an image registration process, and FIG. 20 illustrates another composite thermal image 2000 provided in the same way after performing an image registration process.

Figure 19:
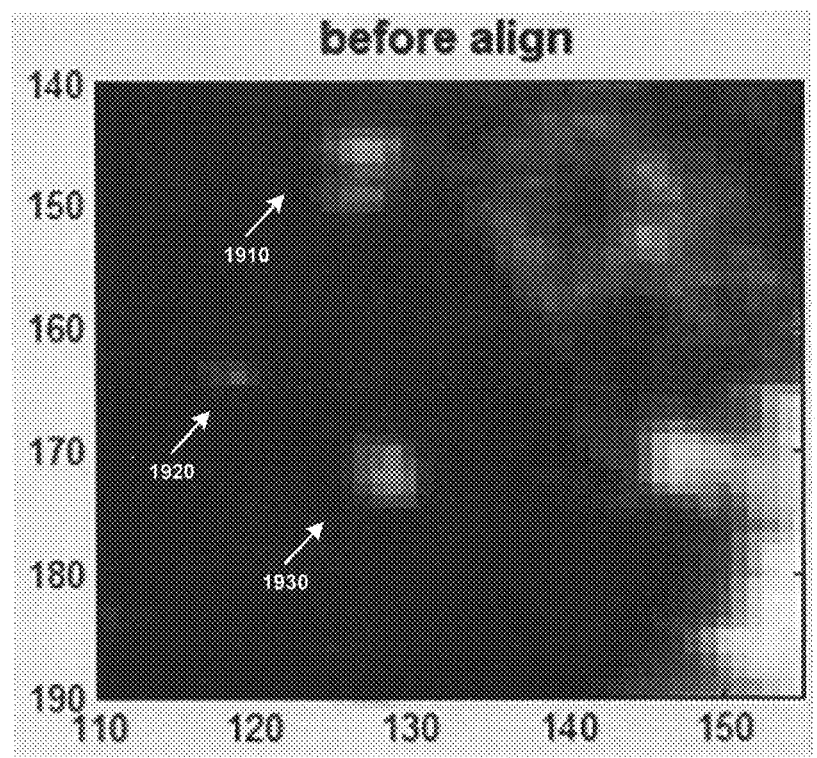
FIG. 19 illustrates a composite thermal image provided by combining a plurality of filtered thermal images without performing an image registration process in accordance with an embodiment of the disclosure.
Figure 20:
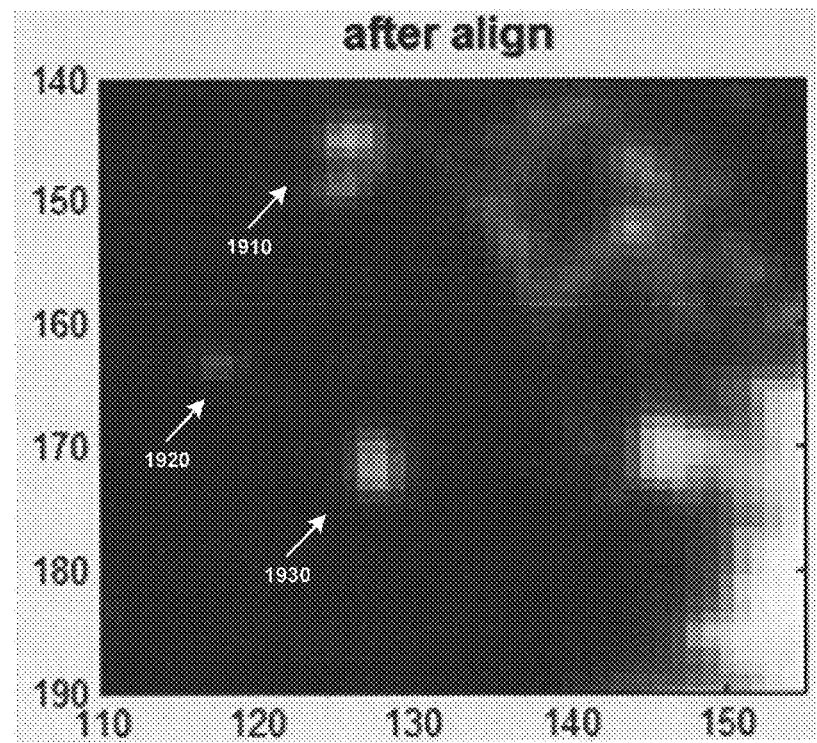
FIG. 20 illustrates a composite thermal image provided by combining a plurality of filtered thermal images after performing an image registration process in accordance with an embodiment of the disclosure.

In comparing FIGS. 19 and 20, image 1900 exhibits subtle blurring, particularly when small particles in regions 1910/1920/1930 and 2010/2020/2030 are compared. By reducing such blurring through image registration, more improved spectral profiles may be obtained, thus providing more reliable identification of materials.

Figure 21:
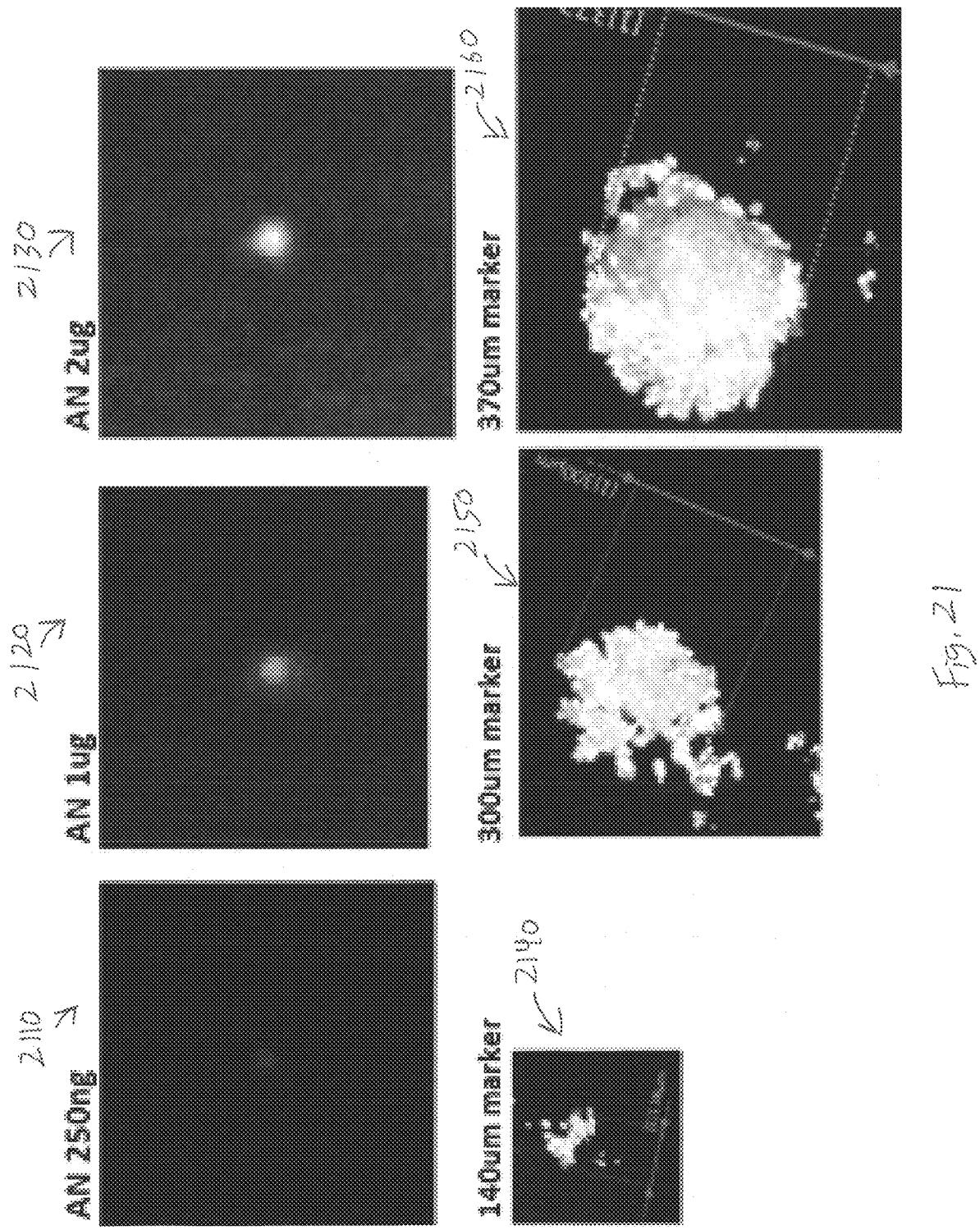
FIG. 21 illustrates various thermal images and corresponding visible light images of different amounts of an imaged material in accordance with an embodiment of the disclosure.

FIG. 21 illustrates various thermal images 2110, 2120, and 2130 and corresponding visible light images 2140, 2150, and 2160 of different amounts of an imaged material in accordance with an embodiment of the disclosure. Thermal images 2110, 2120, and 2130 were obtained by a thermal imager 130/330 having a resolution of 640 by 480 pixels and a 13-mm lens, resulting in an optical resolution of approximately 140 μm. As shown in FIG. 21, using the image registration techniques discussed herein, amounts of ammonium nitrate as small as approximately 250 ng may be detected.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

We claim:

1. A method comprising:
   receiving a test sample;
   conductively heating the test sample to emit thermal infrared radiation from at least a portion of the test sample over a plurality of thermal infrared radiation wavelengths without decomposing the portion of the test sample into a vapor;
   capturing, by an infrared imager, a plurality of thermal infrared images of the portion of the test sample, wherein each infrared image corresponds to a different range of the thermal infrared radiation wavelengths;
   determining, by a processor, a thermal spectral profile of the test sample using the thermal infrared images, wherein the thermal spectral profile comprises a plurality of responses of the test sample provided in the thermal infrared images for the different ranges of the thermal infrared radiation wavelengths;
   comparing, by the processor, the determined thermal spectral profile to a known thermal spectral profile of a material of interest; and
   determining, by the processor, whether the material is present in the test sample based on the comparing.

2. The method of claim 1, further comprising positioning a plurality of filters associated with the different ranges of thermal infrared radiation wavelengths between the test sample and the infrared imager during the capturing.

3. The method of claim 2, wherein the infrared imager comprises a plurality of microbolometers having a spectral sensitivity that varies over the different ranges of thermal infrared radiation wavelengths, wherein the filters are selected to adjust relative throughput of thermal infrared radiation passed by the filters to the microbolometers according to the varying spectral sensitivity.

4. The method of claim 2, wherein the positioning comprises rotating a filter wheel comprising the filters to selectively position the filters.

5. The method of claim 1, wherein the infrared imager comprises a plurality of image capture devices, wherein the capturing is performed by the image capture devices and a plurality of stationary filters associated with the different ranges of thermal infrared radiation wavelengths, wherein each image capture device comprises an array of infrared sensors associated with a different corresponding one of the filters.

6. The method of claim 2, further comprising:
   wherein a first one of the captured thermal infrared images has a first range of thermal infrared radiation wavelengths determined by a first one of the filters;
   wherein a second one of the captured thermal infrared images has a second range of thermal infrared radiation wavelengths determined by a second one of the filters;
   combining the first and second captured thermal infrared images to generate an additional thermal infrared image having a third range of thermal infrared radiation wavelengths different from the first and second ranges; and
   wherein the thermal spectral profile is also determined using the generated additional thermal infrared image.

7. The method of claim 1, wherein the determining a thermal spectral profile comprises processing pixel values and/or emissivities associated with one or more pixel locations of the thermal infrared images.

8. The method of claim 7, wherein the determining whether the material is present is performed in a pixel-wise manner for the one or more pixel locations of the thermal infrared images.

9. The method of claim 1, wherein the test sample is a first test sample, the method further comprising:
   contacting a test surface with a sampling media to capture the first test sample and a second test sample on the sampling media, wherein the first test sample has a lower vapor pressure than the second test sample, wherein the receiving comprises receiving the sampling media in a chamber of the device;
   heating the second test sample to at least partially vaporize;
   passing a vaporized portion of the second test sample to a chemical detector; and
   processing the vaporized portion of the second test sample using the chemical detector to determine its chemical composition.

10. The method of claim 1, wherein the method is performed by a handheld portable detection device comprising a chamber, the infrared imager, and the processor.

11. A device comprising:
    a chamber configured to receive a test sample;
    a heater configured to conductive heat the test sample to emit thermal infrared radiation from at least a portion of the test sample over a plurality of thermal infrared radiation wavelengths without decomposing the portion of the test sample into a vapor;
an infrared imager configured to capture a plurality of thermal infrared images of the portion of the test sample, wherein each infrared image corresponds to a different range of the thermal infrared radiation wavelengths;
a plurality of filters associated with the different ranges of the thermal infrared radiation wavelengths and configured to be positioned between the test sample and the infrared imager during the capture;
a memory comprising instructions; and
a processor configured to execute the instructions to:
   determine a thermal spectral profile of the test sample using the thermal infrared images, wherein the thermal spectral profile comprises a plurality of responses of the test sample provided in the thermal infrared images for the different ranges of the thermal infrared radiation wavelengths,
   compare the determined thermal spectral profile to a known thermal spectral profile of a material of interest, and
   determine whether the material is present in the test sample based on the compared thermal spectral profiles.

12. The device of claim 11, wherein the infrared imager comprises a plurality of microbolometers having a spectral sensitivity that varies over the different ranges of thermal infrared radiation wavelengths, wherein the filters are selected to adjust relative throughput of thermal infrared radiation passed by the filters to the microbolometers according to the varying spectral sensitivity.

13. The device of claim 11, further comprising:
a filter wheel comprising the filters; and
an actuator configured to rotate the filter wheel to selectively position the filters in response to the processor.

14. The device of claim 11, wherein the filters are stationary filters, wherein the infrared imager comprises a plurality of image capture devices, wherein each image capture device comprises an array of infrared sensors associated with a different corresponding one of the filters.

15. The device of claim 11,
wherein a first one of the captured thermal infrared images has a first range of thermal infrared radiation wavelengths determined by a first one of the filters;
wherein a second one of the captured thermal infrared images has a second range of thermal infrared radiation wavelengths determined by a second one of the filters;
wherein the processor is configured to execute the instructions to combine the first and second captured thermal infrared images to generate an additional thermal infrared image having a third range of thermal infrared radiation wavelengths different from the first and second ranges; and
wherein the thermal spectral profile is also determined using the generated additional thermal infrared image.

16. The device of claim 11, wherein the processor is configured to execute the instructions to:
process pixel values and/or emissivities associated with one or more pixel locations of the thermal infrared images to determine the thermal spectral profile.

17. The device of claim 16, wherein the processor is configured to execute the instructions to determine whether the material is present in a pixel-wise manner for the one or more pixel locations of the thermal infrared images.

18. The device of claim 11, wherein:
the test sample is a first test sample;
the chamber is configured to receive a sampling media having the first test sample and a second test sample captured thereon, wherein the first test sample has a lower vapor pressure than the second test sample;
the heater is configured to cause the second test sample to at least partially vaporize; and
the device further comprises a chemical detector configured to receive a vaporized portion of the second test sample and determine a chemical composition of the vaporized portion of the second test sample.

19. The device of claim 11, wherein the device is a handheld portable detection device.

20. The device of claim 11, wherein the material is an oxidizing salt.

* * * * *